(12) United States Patent
Kozlowski

(10) Patent No.: US 7,569,214 B2
(45) Date of Patent: Aug. 4, 2009

(54) METHOD FOR PREPARING WATER-SOLUBLE POLYMER DERIVATIVES BEARING A TERMINAL CARBOXYLIC ACID

(75) Inventor: Antoni Kozlowski, Huntsville, AL (US)

(73) Assignee: Nektar Therapeutics AL, Corporation, Huntsville, AL (US)

( * ) Notice: Subject to any disclaimer, the term of this patent is extended or adjusted under 35 U.S.C. 154(b) by 465 days.

(21) Appl. No.: 10/659,735

(22) Filed: Sep. 9, 2003

(65) Prior Publication Data

US 2005/0036978 A1 Feb. 17, 2005

Related U.S. Application Data

(60) Provisional application No. 60/409,348, filed on Sep. 9, 2002.

(51) Int. Cl.
*A61K 31/74* (2006.01)
*A61K 47/48* (2006.01)

(52) U.S. Cl. ................... 424/78.17; 424/78.31

(58) Field of Classification Search .............. 424/78.18, 424/78.17, 78.31
See application file for complete search history.

(56) References Cited

U.S. PATENT DOCUMENTS

| | | | |
|---|---|---|---|
| 4,079,038 A | | 3/1978 | Choi et al. |
| 4,248,786 A | | 2/1981 | Batz et al. |
| 4,670,417 A | | 6/1987 | Iwasaki et al. |
| 4,943,626 A | | 7/1990 | McGrath et al. |
| 4,957,998 A | | 9/1990 | Heller et al. |
| 5,157,075 A | | 10/1992 | Kanai et al. |
| 5,256,819 A | | 10/1993 | Fried |
| 5,328,955 A | | 7/1994 | Rhee et al. |
| 5,446,090 A | | 8/1995 | Harris |
| 5,483,008 A | | 1/1996 | Sakurai et al. |
| 5,523,479 A | | 6/1996 | Sanders et al. |
| 5,605,976 A | | 2/1997 | Martinez et al. |
| 5,634,971 A | * | 6/1997 | Baker ..................... 106/499 |
| 5,672,662 A | * | 9/1997 | Harris et al. ............. 525/408 |
| 5,681,567 A | | 10/1997 | Martinez et al. |
| 5,763,538 A | * | 6/1998 | Hunter et al. ............ 525/440 |
| 5,824,701 A | | 10/1998 | Greenwald et al. |
| 5,840,900 A | | 11/1998 | Greenwald et al. |
| 5,965,566 A | | 10/1999 | Greenwald et al. |
| 6,011,042 A | | 1/2000 | Greenwald et al. |
| 6,127,355 A | | 10/2000 | Greenwald et al. |
| 6,495,659 B2 | | 12/2002 | Bentley et al. |
| 2001/0021763 A1 | | 9/2001 | Harris |
| 2002/0064546 A1 | | 5/2002 | Harris |
| 2003/0143596 A1 | | 7/2003 | Bentley et al. |

FOREIGN PATENT DOCUMENTS

| WO | WO 9703106 A | 1/1997 |
|---|---|---|
| WO | WO 97/32606 | 9/1997 |
| WO | WO 99/32424 | 7/1999 |
| WO | WO-9932424 * | 7/1999 |
| WO | WO 2004/013205 A1 | 2/2004 |

OTHER PUBLICATIONS

E. J. Corey et al., "A New General Synthetic Route to Bridged Carboxylic Ortho Esters," Tetrahedron Letters (1983), 24(50): pp. 5571-5574.
T. W. Greene et al., "Protective Groups in Organic Synthesis," John Wiley & Sons, Inc.—3rd. Edition (1999), pp. 437-441.
P. Wipf et al., "Synthetic Applications of Ortho Esters," Pure Appl. Chem. (1999), 71(3): pp. 415-421.
C. Yu et al., "Diastereoselective Coupling Reaction of Activated Cyclic Ketene Ortho Ester with Aldehydes Promoted by Lewis Acid Catalyst," J. Org. Chem. (1997), 62: pp. 6687-6689.
Topchiyeva I N, "Synthesis of Biologically Active Polyethylene Glycol Derivatives" Polymer Science USSR, Pergamon Press Ltd. (Oxford, Great Britain), vol. 32 ( No. 5), p. 833-851, 1990.
Veronese F M, "Peptide and Protein Pegylation: A Review of Problems and Solutions," Biomaterials, Elsevier Science Publishers BV (Barking, Great Britain), vol. 22 ( No. 5), p. 405-417, Mar. 2001.
Nektar™—Transforming Therapeutics, Nektar Molecule Engineering: Polyethylene Glycol and Derivatives for Advanced PEGylation, pp. 1-20, (Catalog—2003).
NOF Corporation, "PEG Derivatives, Phospholipid and Drug Delivery Materials for Pharmaceuticals", pp. 1-46, (Catalogue 2003-1st).
NOF Corporation, "PEG Derivatives, Phospholipid and Drug Delivery Materials for Pharmaceuticals", pp. 1-50, (Catalogue 2003-2nd).
Shearwater Polymers, Inc., p. 2-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—2000).
Shearwater Corporation, Polyethylene Glycol and Derivatives for Biomedical Applications, pp. 1-17, (Catalog—2001).
European Patent Office, "Further Examination Report," (Jul. 13, 2007).

* cited by examiner

*Primary Examiner*—Michael G Hartley
*Assistant Examiner*—Blessing M Fubara
(74) *Attorney, Agent, or Firm*—Mark A. Wilson

(57) ABSTRACT

A method is provided for preparing water-soluble polymer derivatives bearing a terminal carboxylic acid or ester thereof. The method involves the hydrolyzing an ortho ester of a water-soluble polymer so as provide the corresponding acid. In addition, the invention provides water-soluble polymers bearing a terminal carboxylic acid or ester thereof, intermediates and reagents useful in carrying out the method, as well as gels, pharmaceutical formulations, conjugates related to the described water-soluble polymer derivatives.

19 Claims, 1 Drawing Sheet

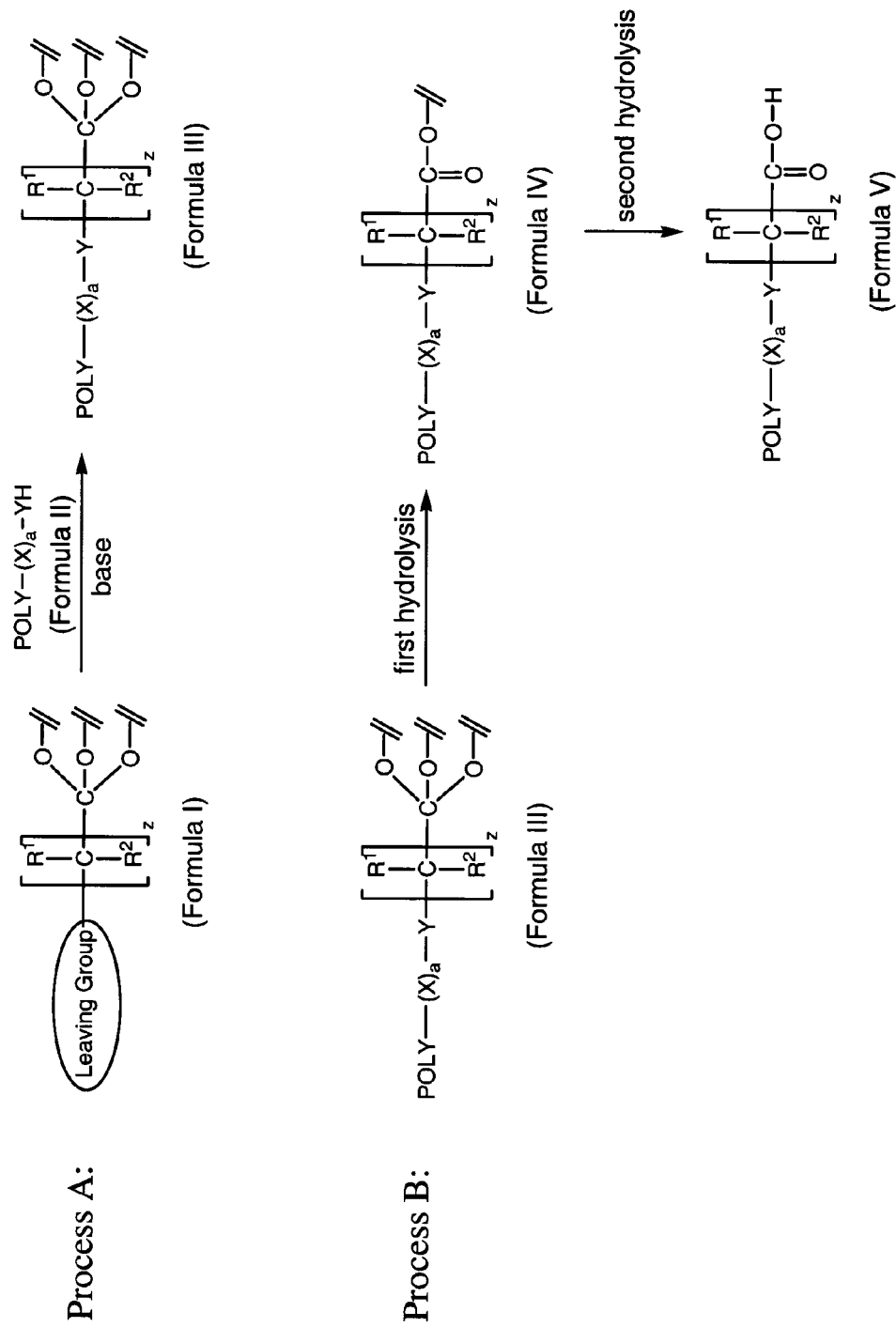

METHOD FOR PREPARING WATER-SOLUBLE POLYMER DERIVATIVES BEARING A TERMINAL CARBOXYLIC ACID

CROSS REFERENCE TO RELATED APPLICATION

This application claims the benefit of priority to provisional application Ser. No. 60/409,348, filed Sep. 9, 2002, which is incorporated herein by reference.

FIELD OF THE INVENTION

The present invention relates generally to novel methods for preparing polymer derivatives that comprise a terminal carboxylic acid or ester thereof. In addition, the invention relates to polymers, conjugates of the polymers, conjugation methods, and intermediates as well as methods for preparing the intermediates. Furthermore, the invention relates to pharmaceutical preparations, synthetic methods, and the like.

BACKGROUND OF THE INVENTION

Conjugating a water-soluble polymer such as poly(ethylene glycol) (or "PEG") to a biologically active agent results in a polymer-active agent conjugate that often has advantageous properties over the corresponding "unconjugated" version of the active agent. Among other advantages, conjugated forms of active agents have increased half-lives and are less immunogenic. When PEG is used to form a polymer-active agent conjugate, the conjugated active agent is conventionally referred to as "PEGylated." Commercially available PEGylated preparations include PEGASYS® PEGylated interferon alpha-2a (Hoffmann-La Roche, Nutley, N.J.), PEG-INTRON® PEGylated interferon alpha-2b (Schering Corp., Kenilworth, N.J.), NEULASTA™ PEG-filgrastim (Amgen Inc., Thousand Oaks, Calif.) and SOMAVERT® pegvisomant (Pfizer, New York, N.Y.). The commercial success of these preparations attests to the value of PEGylation technology.

Polymers bearing a terminal carboxylic acid are useful, either directly or indirectly, in conjugation reactions with active agents and other substances. For example, carboxylic acids can be reacted directly with an amino or hydroxyl group of an active agent, thereby forming a conjugate. Indirectly, polymers bearing a terminal carboxylic acid (which acts as a reactive electrophilic group) can serve as a convenient starting material for preparing other polymer derivatives bearing functional groups other than carboxylic acids. Polymers bearing a functional group other than a carboxylic acid can then form conjugates with active agents bearing a suitable reactive group.

Methods for preparing certain water-soluble polymers bearing a terminal carboxylic acid have been described. For example U.S. Pat. No. 5,681,567 describes reacting a poly(alkylene oxide) with a tertiary-alkyl haloacetate to thereby form a tertiary-alkyl ester of a poly(alkylene oxide) carboxylic acid. Schematically, the reaction using a tertiary-alkyl chloroacetate can be represented as follows:

poly(alkylene oxide)—OH +

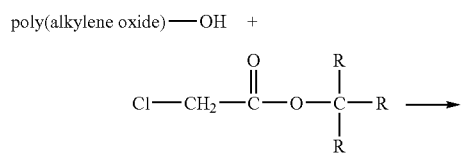

-continued

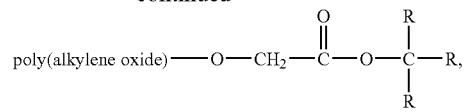

wherein each R is alkyl. Subsequent reaction of the ester with an acid removes the tertiary alkyl moiety, which yields the corresponding acetic acid. This method, however, only results in polymers bearing a terminal acetic acid moiety. Polymer derivatives synthesized to terminate in an acetic acid moiety are sometimes referred to as "carboxymethylated" polymers.

Polymer derivatives bearing a terminal acetic acid can be further reacted to form polymer derivates bearing other reactive moieties. For example, a succinimidyl ester of carboxymethyl PEG can be formed. This succinimidyl ester, however, is so reactive that it hydrolyzes almost immediately in aqueous solution. Thus, the practical utility of PEG derivatives bearing a terminal acetic acid moiety can be low given the overly reactive nature of these derivatives.

Another method for preparing certain water-soluble polymers bearing a terminal carboxylic acid derivative is described in U.S. Pat. No. 5,523,479. In this approach, a moiety having a molecular weight of from 32 to 6000 and having from one to 6 hydroxyl groups is reacted with a tertiary alkyl ester of a beta-unsaturated carboxylic acid to yield a product having a terminal ester. Schematically, the reaction in can be represented as follows (the moiety is presented as having a single hydroxyl group and the tertiary alkyl ester of a beta-unsaturated carboxylic acid is represented by tertiary alkyl ester of acrylic acid)

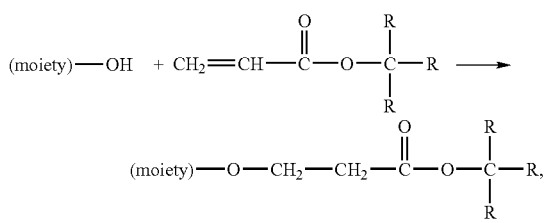

wherein R is alkyl. A subsequent hydrolytic step transforms the ester into the corresponding propanoic acid.

While providing polymer derivatives that lack a reactive acetic acid moiety, this method suffers from other drawbacks. First, the method inherently provides for only propanoic acid derivates. In addition, the best reported conversion of the hydroxyl group to the ester is less than 85%. Finally, only moieties having a molecular weight between 32 and 6000 are described in connection with carrying out the method. There remains a need, however, to provide a method that can prepare acids other than propanoic acid derivatives, result in conversion to an ester and/or acid of greater than 85%, and be used with moieties having a molecular weight outside of the range of 32 to 6000.

U.S. Pat. No. 5,672,662, discloses PEG derivatives having a terminal propanoic acid or butanoic acid moiety that can be used to prepare active esters suitable for conjugation to proteins or other molecules bearing amino groups. The active esters described in U.S. Pat. No. 5,672,662 exhibit greater stability in solution than active esters of carboxymethylated PEG, and are thus better suited for conjugation to biologically active molecules. The method described for preparing these PEG derivatives having a terminal propanoic or butanoic moiety, however, involves numerous steps and only results in about 80% substitution into the carboxylic acid moiety. As a consequence, the method described in U.S. Pat. No. 5,672,662 requires expensive and time-consuming purification steps in order to provide a pharmaceutical grade product.

Thus, there remains a need in the art for improved methods for preparing polymer derivatives bearing a terminal carboxylic acid. In addition, there continues to be a need to provide novel polymers bearing a carboxylic acid moiety that are useful for conjugation reactions and further functionalization. The present invention addresses these and other needs in the art by providing, inter alia, novel methods for the efficient preparation of polymer derivatives bearing a terminal carboxylic acid.

SUMMARY OF THE INVENTION

Accordingly, it is a primary object of this invention to provide a method for making a carboxylic acid of a water-soluble polymer comprising the steps of (a) reacting a water-soluble polymer segment having at least one alkoxide ion or thiolate ion with an ortho ester comprised of a suitable leaving group to form an ortho ester of a water-soluble polymer; and (b) subjecting the ortho ester of a water-soluble polymer formed in step (a) to one or more hydrolysis steps so as to provide the corresponding carboxylic acid of a water-soluble polymer.

It is another object of the invention to provide an ortho ester useful in the method for making the carboxylic acid of the water-soluble polymer. Thus, this object of the invention comprises carrying out step (a) recited in the immediately preceding paragraph.

It is yet another object of the invention to provide a carboxylic acid of a water-soluble polymer prepared by a method described herein.

It is a further object of the invention to provide a carboxylic acid or ester thereof of a water-soluble polymer.

It is still another object of the invention to provide an ortho ester of a water-soluble polymer.

It is still yet another object of the invention to provide gels, conjugates, and pharmaceutical compositions comprising a polymer described herein.

It is another object of the invention to provide methods for preparing each of the gels, conjugates, and pharmaceutical compositions described herein.

It is a further object of the invention to provide methods for administering each of the gels, conjugates, and pharmaceutical compositions described herein, comprising the step of delivering the preparation to a patient.

Additional objects, advantages and novel features of the invention will be set forth in the description that follows, and in part, will become apparent to those skilled in the art upon the following, or may be learned by practice of the invention.

In one embodiment of the invention then, an ortho ester of a water-soluble polymer is provided. Among other uses, the ortho ester has utility as an intermediate in the synthesis of a water-soluble polymer bearing a terminal carboxylic acid group. The ortho ester of the water-soluble polymer preferably comprises the following structure:

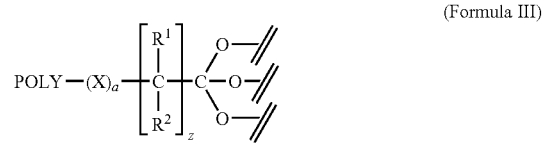

(Formula III)

wherein:

POLY is a water-soluble polymer segment;

(a) is either zero or one;

X, when present, is a spacer moiety;

(z) is an integer from 1 to 24;

$R^1$, in each occurrence, is independently H or an organic radical selected from the group consisting of alkyl, substituted alkyl, alkenyl, substituted alkenyl, alkynyl, substituted alkynyl, aryl, and substituted aryl;

$R^2$, in each occurrence, is independently H or an organic radical selected from the group consisting of alkyl, substituted alkyl, alkenyl, substituted alkenyl, alkynyl, substituted alkynyl, aryl, and substituted aryl; and

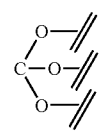

represents a residue of a ortho ester moiety.

In another embodiment, the present invention provides a method for making an ortho ester of a water-soluble polymer. The method comprises the step of reacting, in the presence of a base, a water-soluble polymer segment having at least one hydroxyl or thiol group with an ortho ester comprised of a suitable leaving group. It is preferred that the water-soluble polymer segment has at least one hydroxyl group and lacks any thiol groups.

Typically, although not necessarily, the ortho ester comprising a suitable leaving group is comprised of the following structure:

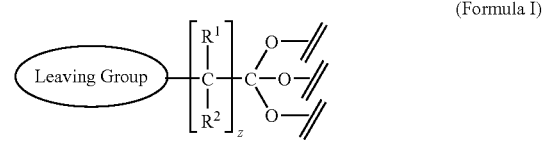

(Formula I)

wherein:

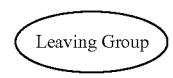

is the suitable leaving group;

(z) is an integer from 1 to 24;

$R^1$, in each occurrence, is independently H or an organic radical selected from the group consisting of alkyl, substituted alkyl, alkenyl, substituted alkenyl, alkynyl, substituted alkynyl, aryl, and substituted aryl;

$R^2$, in each occurrence, is independently H or an organic radical selected from the group consisting of alkyl, substituted alkyl, alkenyl, substituted alkenyl, alkynyl, substituted alkynyl, aryl, and substituted aryl; and

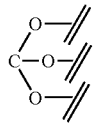

represents a residue of a ortho ester moiety.

In a further embodiment of the invention, a method for making a carboxylic acid of a water-soluble polymer is provided. The method comprises the step of subjecting an ortho ester of a water-soluble polymer to one or more hydrolysis steps so as to provide the corresponding carboxylic acid of a water-soluble polymer. Although a single hydrolysis step can be performed, it is preferred that two sequential hydrolysis steps are performed. Exemplary double hydrolysis steps include an initial base hydrolysis step followed by a second base hydrolysis step and an initial acid hydrolysis step followed by a base hydrolysis step.

In another embodiment, the invention provides a carboxylic acid of a water-soluble polymer prepared by the method. In this regard, polymers such as those having the following structure can be prepared:

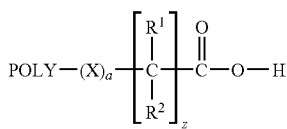

(Formula V)

wherein:

POLY is a water-soluble polymer segment;

(a) is either zero or one;

X, when present, is a spacer moiety;

(z) is an integer from 1 to 24;

$R^1$, in each occurrence, is independently H or an organic radical selected from the group consisting of alkyl, substituted alkyl, alkenyl, substituted alkenyl, alkynyl, substituted alkynyl, aryl, and substituted aryl; and $R^2$, in each occurrence, is independently H or an organic radical selected from the group consisting of alkyl, substituted alkyl, alkenyl, substituted alkenyl, alkynyl, substituted alkynyl, aryl, and substituted aryl.

The corresponding ester versions of these acids are also included wherein the terminal carboxylic moiety "—C(O)OH" of the polymer is replaced by "—C(O)OR$^3$" wherein R$^3$ is defined as an organic radical selected from the group consisting of alkyl, substituted alkyl, alkenyl, substituted alkenyl, alkynyl, substituted alkynyl, aryl, and substituted aryl.

Exemplary polymers bearing a terminal carboxylic acid or ester thereof include those having the following structure:

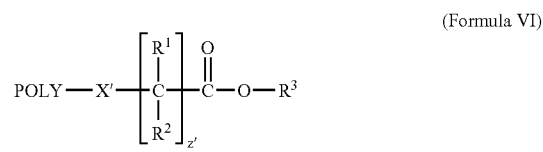

(Formula VI)

wherein:

POLY is a water-soluble polymer segment;

X' is a spacer moiety with the proviso that when the spacer moiety is only one atom, the one atom is not O or S;

(z') is an integer from 3 to 24;

$R^1$, in each occurrence, is independently H or an organic radical selected from the group consisting of alkyl, substituted alkyl, alkenyl, substituted alkenyl, alkynyl, substituted alkynyl, aryl, and substituted aryl;

$R^2$, in each occurrence, is independently H or an organic radical selected from the group consisting of alkyl, substituted alkyl, alkenyl, substituted alkenyl, alkynyl, substituted alkynyl, aryl, and substituted aryl; and $R^3$ is H or an organic radical selected from the group consisting of alkyl, substituted alkyl, alkenyl, substituted alkenyl, alkynyl, and substituted alkynyl. Thus, it is preferred that $R^3$ is nonaromatic.

For any structure comprising a water-soluble polymer segment, any polymer that is water-soluble can be used and the invention is not limited in this regard. Preferred water-soluble polymer segments, however, are terminally end-capped on one terminus. In addition, water-soluble polymer segments having a mass average molecular mass of less than about 100,000 Daltons are preferred.

BRIEF DESCRIPTION OF THE DRAWING

FIG. 1 is a schematic representation of one approach for preparing a water-soluble polymer bearing a terminal carboxylic acid according to the invention.

DETAILED DESCRIPTION OF THE INVENTION

Overview and Definitions

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

It must be noted that, as used in this specification and the claims, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes—depending upon whether or not the terminal oxygen(s) has been displaced—the following similar structures "—CH$_2$CH$_2$—O(CH$_2$CH$_2$O)$_m$—CH$_2$CH$_2$—" and "—(CH$_2$CH$_2$O)$_m$—" where (m) is 2 to 4000. When the PEG further comprises a linker moiety (to be described in greater detail below), the atoms comprising the linker, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," and the like, to be described in greater detail below.

The terms "end-capped" or "terminally capped" are used interchangeably herein to refer to a terminal or endpoint of a polymer that terminates with an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled to of interest can be determined by using a suitable detector. Such labels include, without limitation, fluorescers, chemiluminescers, moieties used in enzyme labeling, calorimetric (e.g., dyes), metal ions, radioactive moieties, and the like. Suitable detectors include photometers, films, spectrometers, and the like.

"Non-naturally occurring" with respect to a polymer or water-soluble polymer segment means a polymer that in its entirety is not found in nature. A non-naturally occurring polymer or water-soluble polymer segment may, however, contain one or more subunits or portions of a subunit that are naturally occurring, so long as the overall polymer structure is not found in nature.

The term "water soluble" as in a "water-soluble polymer segment" and "water-soluble polymer" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

"Molecular mass" in the context of a water-soluble, non-naturally occurring polymer of the invention such as PEG, refers to the nominal average molecular mass of a polymer, typically determined by size exclusion chromatography, light scattering techniques, or intrinsic velocity determination in 1,2,4-trichlorobenzene. The polymers of the invention are typically polydisperse, possessing low polydispersity values of preferably less than about 1.2, more preferably less than about 1.15, still more preferably less than about 1.10, yet still more preferably less than about 1.05, and most preferably less than about 1.03.

"Thiol derivative," in the context of a water-soluble polymer, means a polymer having at least one terminus that is a thiol group (—SH), a thiolate (—S$^-$) or a protected thiol, that is to say, a thiol group in its protected form. Typical thiol protecting groups include thioether, thioester, or disulfide. Exemplary protecting groups for thiols can be found in Greene et al., "PROTECTIVE GROUPS IN ORGANIC SYNTHESIS," 3$^{rd}$ Edition, John Wiley and Sons, Inc., New York, 1999.

As used herein, the term "carboxylic acid" as in a "carboxylic acid" derivative is a moiety having a

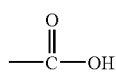

functional group [also represented as a "—COOH" or —C(O)OH]. Unless the context clearly dictates otherwise, the term carboxylic acid includes not only the acid form, but corresponding esters and protected forms as well. Reference is again made to Greene et al. supra with respect suitable protecting groups for carboxylic acids.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The term "spacer" or "spacer moiety" is used herein to refer to an atom or a collection of atoms optionally used to link interconnecting moieties such as a terminus of a water-soluble polymer segment and an electrophile. The spacer moieties of the invention may be hydrolytically stable or may include a physiologically hydrolyzable or enzymatically degradable linkage.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, iso-butyl, and tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like. "Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

The terms "active agent" and "biologically active agent" are used interchangeably herein and are defined to include any agent, drug, compound, composition of matter or mixture that provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

"Multifunctional" in the context of a polymer of the invention means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

A basic or acidic reactant described herein includes neutral, charged, and any corresponding salt forms thereof.

The term "patient," refers to a living organism suffering from or prone to a condition that can be prevented or treated by administration of a conjugate as provided herein, and includes both humans and animals.

"Optional" and "optionally" mean that the subsequently described circumstance may or may not occur, so that the description includes instances where the circumstance occurs and instances where it does not.

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the ionic form is used when the halogen exists in its independent ionic form (e.g., such as when a leaving group leaves a molecule).

In the context of the present discussion, it should be recognized that the definition of a variable provided with respect to one structure or formula is applicable to the same variable repeated in a different structure, unless the context dictates otherwise. Thus, for example, the definition of "POLY," "a spacer moiety," "(z)," and so forth with respect to an ortho ester of a water-soluble polymer is equally applicable to a water-soluble polymer bearing a carboxylic acid.

The Method

The present methods for preparing a carboxylic acid of a water-soluble polymer have several advantages. As shown herein, for example, water-soluble polymers bearing a terminal carboxylic acid moiety can be provided in high purity. Although prior art approaches result in relatively low purity, conversions of at least about 85%, more preferably at least about 90%, still more preferably at least about 95%, and most preferably at least about 98% conversion of a precursor molecule into the corresponding carboxylic acid derivative are shown herein. Because water-soluble polymers bearing a terminal carboxylic acid moiety can now be provided in relatively high purity, expensive and time consuming purification steps are reduced or eliminated entirely.

Another advantage of the current methods for preparing a carboxylic acid of water-soluble polymer is the ability to prepare a larger range of structurally diverse derivatives. Previously described methods necessarily resulted in, for example, certain acetic acid or carboxymethylated derivatives (see U.S. Pat. No. 5,681,567), certain propanoic acid derivatives (see U.S. Pat. Nos. 5,523,479 and 5,672,662), and certain butanoic acid derivatives (see U.S. Pat. No. 5,672,662). These previously described derivatives are necessarily limited to certain structures since the methods used to create them rely on a relatively narrow palette of possible reagents suitable for use with these methods. Advantageously, the present methods can be used with a relatively large number of reagents, thereby greatly expanding the range of possible structures.

A first method is thus provided to form an ortho ester of a water-soluble polymer, which serves as a useful intermediate in further carrying out a step for subsequent formation of a water-soluble polymer bearing a terminal carboxylic acid. Process A as shown in FIG. 1, depicts one approach for carrying out this first method. One approach for the subsequent formation of a water-soluble polymer bearing a terminal carboxylic acid (Formula V) is shown as process B in FIG. 1. Provided only for assistance in better understanding a synthetic method presented herein, FIG. 1 in no way should be construed as limiting the invention. The various formulae shown in FIG. 1 are described in more detail below.

Initially, the method for forming an ortho ester of a water-soluble polymer comprises the step of reacting a water-soluble polymer segment having at least one alkoxide ion or thiolate ion with an ortho ester comprised of a suitable leaving group (i.e., an ortho ester-containing molecule comprised of a suitable leaving group). Conveniently, and with reference to FIG. 1, the water-soluble polymer segment having at least one alkoxide ion or thiolate ion is prepared by combining a water-soluble polymer having at least one hydroxyl or thiol group (Formula II) in the presence of a suitable base. An ortho ester comprising a suitable leaving group (Formula I) is allowed to react with a water-soluble polymer having at least one hydroxyl or thiol group (Formula II) to form an ortho ester comprised of a suitable leaving group (Formula III).

The base used in this approach, however, must be one that will form an alkoxide (i.e., R—O$^-$) or thiolate (i.e., R—S$^-$) of the water-soluble polymer having at least one hydroxyl or thiol group, respectively. Thus, for example, the base transforms POLY-(X)$_a$—OH into POLY-(X)$_a$—O$^-$ and POLY-(X)$_a$—SH into POLY-(X)$_a$—S$^-$. It is further believed that the water-soluble polymer, now bearing an alkoxide or thiolate moiety, in turn reacts via a S$_N$2 reaction mechanism with the ortho ester having a suitable leaving group (Formula I). As will be recognized by those of ordinary skill in the art, this approach corresponds to Williamson ether synthesis, and the principles and techniques generally used in a Williamson ether synthesis are applicable here as well.

Nonlimiting examples of bases suitable to form an alkoxide of an alcohol or a thiolate of a thiol-containing compound include sodium, sodium hydroxide, potassium, potassium hydroxide, sodium hydride, potassium hydride, sodium methoxide, potassium methoxide, sodium tert-butoxide, potassium tert-butoxide, sodium carbonate, and potassium carbonate. Preferred bases for use in accordance with this step, however, include those selected from the group consisting of sodium, potassium, sodium hydride, potassium hydride, sodium methoxide, potassium methoxide, sodium tert-butoxide, and potassium tert-butoxide.

In addition, the water-soluble polymer segment having at least one alkoxide ion or thiolate ion can conveniently be provided via a polymerization reaction, as will be discussed in more detail below. In this approach for providing the water-soluble polymer segment, it is preferred that the water-soluble polymer segment has at least one alkoxide ion.

Generally, although not necessarily, an excess of the ortho ester comprising a suitable leaving group (Formula I) is allowed to react with the water-soluble polymer bearing at least one alkoxide ion or thiolate ion (Formula II). Typically, the amount of the ortho ester comprising a suitable leaving group (Formula I) represents at least a molar equivalent to the number available hydroxyl or thiol groups in the water-soluble polymer having at least one hydroxyl or thiol group (Formula II). Heterofunctional polymer species (i.e., species bearing two or more different terminal functional groups) can be prepared by using nonstoichiometric amounts of the ortho ester comprising a suitable leaving group (Formula I). That is, heterofunctional species are formed when the total number of moles of available hydroxyl or thiol groups on the water-soluble polymer having at least one hydroxyl or thiol group (Formula II) exceeds the total number of moles of the ortho ester comprising a suitable leaving group (Formula I) added to the reaction.

The ortho ester of the water-soluble polymer (Formula III) can be prepared by other means and the invention is not limited simply to process A as depicted in FIG. 1. For example, an ortho ester comprising at least one initiator site suitable for polymerization can be used to grow one or more water-soluble polymer segments. Using this approach, an ortho ester comprising at least one initiator site (e.g., an alkoxide moiety) and a reactive monomer (e.g., ethylene oxide) are combined and the reaction is allowed to proceed until all of the reactive monomer is exhausted or the reaction is terminated by, for example, neutralizing the reaction medium. The last reactive monomer, e.g., ethylene oxide, added to the growing chain may conveniently provide an alkoxide ion or thiolate ion for subsequent reaction with, for example, an ortho ester comprised of a suitable leaving group.

Specifically, the following steps can be followed in order to build the water-soluble polymer segment directly onto an ortho ester comprising at least one initiator site: (i) providing an ortho ester comprising at least one active anionic site suitable for initiating polymerization; (ii) contacting the anionic site of the ortho ester with a reactive monomer capable of polymerizing, to thereby initiate polymerization of the reactive monomer onto the ortho ester precursor; (iii) adding addition reactive monomers to the ortho acid precursor to form one or more polymer chain(s); (iv) allowing said contacting to continue until a desired length of the polymer chain(s) is reached; and (v) terminating the reaction to achieve an ortho ester of a water-soluble polymer.

Any reactive monomer can be used to "grow" the polymer chain(s) so long as the resulting polymer chain is water soluble. It is particularly preferred, however, that the reactive monomer is ethylene oxide, thereby providing poly(ethylene oxide) chain(s). Growth of the polymer chain(s), including the initial attachment of the reactive monomer to the initiator site, can be effected through, for example, an alkoxide ion (i.e., R—O$^-$). These and other techniques are known to those of ordinary skill in the art and are referenced in, for example, Odian, Chap. 7, Principles of Polymerization, 3$^{rd}$ Ed., McGraw-Hill, 1991.

Growth of the polymer chain(s) continues until the desired molecular weight is achieved. Thus, for example, neutralizing the reaction medium halts the growth of the polymer chain(s). In addition, adding a specific weight or amount of the reactive monomer and allowing the polymerization to proceed until all reactive monomer is exhausted results in a polymer chain having a corresponding molecular weight. Once the polymer chain(s) are formed, an end-capping group can be added using conventional techniques. For example, an alkyl halide (e.g., methyl halide or methyl p-toluenesulfonate) can be reacted with the exposed terminal (the terminal distal to the ortho ester functionality) of the polymer chain.

A related, although different, polymerization approach can also be used to provide an ortho ester of a water-soluble polymer. In this related approach, the polymerization is carried out to first form a polymer chain that can be subsequently transformed into the ortho ester derivative. Thus, for example, an alkoxy alcoholate salt such as sodium 2-methoxy ethanolate (Na$^+$:$^{-OCH}$$_2$CH$_2$OCH$_3$) can initiate polymerization of ethylene oxide by essentially following the same procedure outlined above. Assuming that the final monomer added to the polymer chain leaves a reactive group such as an alkoxide (as in the case of ethylene oxide), the polymer chain can then be reacted with an ortho ester comprising a suitable leaving group. To the extent that the polymer chain does not leave a group (e.g., an alkoxide) suitable for direct attachment to an ortho ester-containing reagent, additional modifications to the polymer chain can be made such that an ortho ester can be attached.

Use of an alkoxy alcoholate salt as an initiator of the polymer results in an ortho ester of a water-soluble polymer comprising a single ortho ester functionality. Polymers comprising two ortho esters functionalities (a bifunctional polymer) can result when dialcoholate salts (e.g. 2Na$^+$:$^-$OCH$_2$CH$_2$O$^-$) are used in place of alkoxy alcoholate salts. As described above, an optional capping step can also be performed with this polymerization approach.

Returning to FIG. 1, the ortho ester of a water-soluble polymer (Formula III) can be converted into a water-soluble polymer bearing a terminal carboxylic (Formula V). The conversion into the corresponding carboxylic acid derivative is advantageously accomplished efficiently and in high yield by performing one or more hydrolysis steps. Either acid-catalyzed hydrolysis or acid-catalyzed hydrolysis followed by base-promoted hydrolysis can provide the water-soluble polymer bearing a terminal carboxylic acid (Formula V).

Although conversion into the carboxylic acid can be carried out in a single hydrolysis step via acid-catalyzed hydrolysis, it is believed that this single hydrolytic approach is inefficient in terms of time. It has been found that two hydrolysis steps, however, increases the speed for converting the carboxylic acid from the corresponding ortho ester.

In a two hydrolysis step approach, a first hydrolysis step results in the ortho ester functionality being transformed into an ester (Formula IV). A second hydrolysis step, in turn, converts the ester (Formula IV) to the corresponding polymer bearing a terminal carboxylic acid (Formula IV).

The first hydrolysis step should be acid-catalyzed hydrolysis. The ortho ester functionality can be cleaved by mild aqueous acidic conditions such as p-toluenesulfonic acid (p-TsOH) and pyridine in water, and NaHSO$_4$ and 1,2-dimethoxyethane (DME) in water at 0° C. for 20 minutes. See Just et al. (1983) *Can. J. Chem.* 61:712 and Corey et al. (1986) *Tetrahedron Lett.* 27:2199, respectively. Examples of other acids suitable for use in acid-catalyzed hydrolysis include, without limitation, hydrofluoric acid (HF), hydrochloric acid (HCl), hydrobromic acid (HBr), hydroiodic acid (HI), nitric acid (HNO$_3$), perchloric acid (HClO$_4$), sulfuric acid (H$_2$SO$_4$), acetic acid (CH$_3$CO$_2$H), carbonic acid H$_2$CO$_3$, phosphoric acid (H$_3$PO$_4$), oxalic acid (H$_2$C$_2$O$_4$), and formic acid (HCOOH).

The second hydrolysis step is typically a base-promoted hydrolysis step. The ester (Formula IV) of the first hydrolysis step is treated with a base. For base-promoted hydrolysis, the ortho ester functionality is treated with any aqueous base, such as lithium hydroxide (LiOH), sodium hydroxide (NaOH), potassium hydroxide (KOH), rubidium hydroxide (RuOH), cesium hydroxide [Cs(OH)$_2$], strontium hydroxide [Sr(OH)$_2$], barium hydroxide [Ba(OH)$_2$], ammonium hydroxide (NH$_4$OH), magnesium hydroxide [Mg(OH)$_2$], calcium hydroxide [Ca(OH)$_2$], sodium acetate (NaCH$_3$CO$_2$), potassium acetate (KCH$_3$CO$_2$), sodium carbonate (Na$_2$CO$_3$), potassium carbonate (K$_2$CO$_3$), lithium carbonate (Li$_2$CO$_3$), sodium phosphate (Na$_3$PO$_4$), potassium phosphate (K$_3$PO$_4$), sodium borate (Na$_3$BO$_4$), potassium borate (Li$_3$PO$_4$), and so forth.

The first, and optional second hydrolysis steps can be carried out under increased heat in order to increase the rate reaction.

The steps of the method take place in an appropriate solvent. One of ordinary skill in the art can determine whether any specific solvent is appropriate for any given reaction. Typically and in particular with respect processes A and B as shown in FIG. 1, however, the solvent is preferably a nonpolar solvent or a polar aprotic solvent. Nonlimiting examples of nonpolar solvents include benzene, xylene, dioxane, tetrahydrofuran (THF), t-butyl alcohol and toluene. Particularly preferred nonpolar solvents include toluene, xylene, dioxane, tetrahydrofuran, and t-butyl alcohol. Exemplary polar aprotic solvents include, but are not limited to, DMSO (dimethyl sulfoxide), HMPA (hexamethylphosphoramide), DMF (dimethylformamide), DMA (dimethylacetamide), NMP (N-methylpyrrolidinone).

With respect to hydrolysis, in particular, water is a preferred solvent, although aqueous mixtures of water with other solvents such as water and tetrahydrofurn, water and 1,2-dimethylethane, water and diglyme, as well as other aqueous-containing solvents can be used.

Optionally, the method further comprises the step of recovering the carboxylic acid of the water-soluble polymer. Art-known techniques can be used to recover the polymer and include, for example, precipitating the polymer from solution. The precipitate can then be collected and optionally filtered and/or dried. These and other techniques can be used to isolate and recover the carboxylic acid of the water-soluble polymer.

In addition, the method optionally includes the step of further purifying the carboxylic acid of the water-soluble polymer. Such a purifying step, however, is generally not required given the relatively high degree of converting a precursor (e.g., ortho ester of a water-soluble polymer) into the corresponding carboxylic acid. In any event, art-known techniques such chromatography can be used to purify the polymer.

The acids so produced according to the present method are substantially pure and can be prepared in a one-pot approach. By pure, it is meant that preferably greater than at least about 85%, more preferably greater than at least about 90%, still more preferably greater than at least about 95%, and most preferably greater than at least about 98% of the total amount (either by weight or molar basis) of the water-soluble polymer bearing a hydroxyl or thiol group is converted to water-soluble polymer bearing a terminal carboxylic acid.

The Ortho Ester of a Water-Soluble Polymer

As indicated above, the method requires use of an ortho ester comprising a suitable leaving group. Structurally, the ortho ester comprises a "branching carbon atom." This branching carbon atom is a carbon atom covalently attached to three oxygen atoms, which, in turn, are typically each covalently attached to, for example, an alkyl moiety. Given the tetravalent nature of carbon, the branching carbon atom also comprises a fourth covalent attachment. In the case of the present ortho esters of the invention used to make alkanoic acids, the fourth covalent attachment of the branching carbon atom is to a substituted or unsubstituted carbon chain, such as an alkylene chain. Finally, a suitable leaving group is attached, either directly or though a spacer moiety, at the end of the carbon chain that is not attached to the branching carbon atom.

An exemplary structure of an ortho ester comprising a suitable leaving group is provided below.

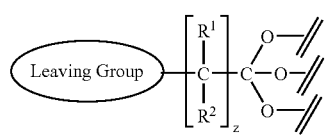

(Formula I)

wherein:

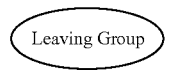

is the suitable leaving group;

(z) is an integer from 1 to 24;

$R^1$, in each occurrence, is independently H or an organic radical selected from the group consisting of alkyl, substituted alkyl, alkenyl, substituted alkenyl, alkynyl, substituted alkynyl, aryl, and substituted aryl;

$R^2$, in each occurrence, is independently H or an organic radical selected from the group consisting of alkyl, substituted alkyl, alkenyl, substituted alkenyl, alkynyl, substituted alkynyl, aryl, and substituted aryl; and

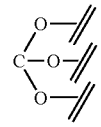

represents a residue of a ortho ester moiety.

With respect Formula I, the suitable leaving group is any atom or group of atoms that can leave the carbon atom to which it is attached. Specifically, a suitable leaving group is one that can be displaced by an approaching nucleophile. Those of ordinary skill in the art can determine what atom or group of atoms can serve as a suitable leaving group. In addition, routine experimentation can identify whether any specific atom or group of atoms can serve as a suitable leaving group. For example, a proposed leaving group on a molecule comprising an ortho ester can be tested by reacting the ortho ester with a water-soluble polymer segment having a hydroxyl group; the proposed leaving group is a suitable leaving group if detectable amounts of the corresponding ortho ester of the water-soluble polymer are formed.

Preferred suitable leaving groups include those that are primary (e.g., a primary halo), although leaving groups that are secondary may also be used. Examples of suitable leaving groups include halogens and sulfonate esters. Among the halogens, bromo, chloro, iodo, and fluoro are preferred, with bromo and chloro being particularly preferred halogen-type leaving groups. With respect to sulfonate esters, methanesulfonate, trifluoromethanesulfonate, trichloromethanesulfonate, 2,2,2-trifluoroethanesulfonate, 2,2,2-trichloroethanesulfonate, and para-toluenesulfonate are particularly preferred, although other sulfonate esters and similarly constituted leaving groups known to those of ordinary skill in the art can be used as well.

With respect to the specific ortho ester functionality associated with Formula I, any ortho ester functionality can be used and the invention is not limited in this regard. An exemplary ortho ester functionality, however, is comprised of the following structure:

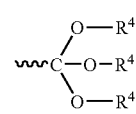

wherein each $R^4$ is an organic radical independently selected from the group consisting of alkyl, substituted alkyl, alkenyl, substituted alkenyl, alkynyl, substituted alkynyl, aryl, substituted aryl, and one or more atoms that combine with another $R^4$ or the remaining $R^4$ moieties to form a ringed structure.

The ortho ester functionality can be acyclic, i.e., lacking a ringed structure. When acyclic, it is preferred that each $R^4$ in the above-defined structure is independently a $C_{1-6}$ alkyl (e.g., methyl, ethyl or propyl) or substituted $C_{1-6}$ alkyl. In addition, the ortho ester functionality can be in form of a "cyclic" or "ringed" structure. In the present context, the term "cyclic" will be understood to include monocyclic, bicyclic, and polycyclic structures. In cyclic versions, the ortho ester functionality is preferably in the form of a substituted or unsubstituted heterocyclic ring comprising from about 6 to about 14 atoms. Preferred substituents for the heterocyclic ring include $C_{1-6}$ alkyl, such as methyl or ethyl, or substituted $C_{1-6}$ alkyl. Examples of such preferred cyclic structures include the following bridged heterocyclic rings:

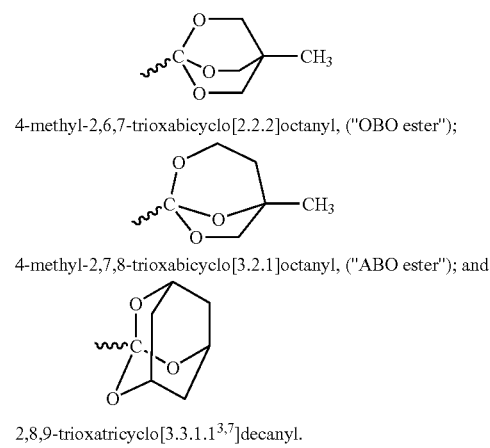

4-methyl-2,6,7-trioxabicyclo[2.2.2]octanyl, ("OBO ester");

4-methyl-2,7,8-trioxabicyclo[3.2.1]octanyl, ("ABO ester"); and 2,8,9-trioxatricyclo[3.3.1.1$^{3,7}$]decanyl.

One of ordinary skill in the art can readily envision other cyclic structures that comprise other ortho ester structures (both cyclic and acyclic).

As can bee seen with respect to Formula I, the ortho ester comprising a suitable leaving group comprises a carbon chain of (z) carbons defined by the following structure:

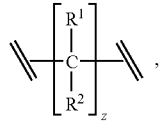

wherein (z), each $R^1$ and each $R^2$ are as previously defined. Preferably, however, (z) is equal to one, two, three, four or five.

The carbon chain can be a simple, straight chain of carbon atoms. Simple, straight carbon chains are those in which each $R^1$ and $R^2$ is defined as hydrogen. In addition, the carbon chain may comprise one or more carbon-carbon double and/or triple bonds. Moreover, the carbon chain can be singly branched wherein one of $R^1$ and $R^2$ is defined as an atom or group of atoms other than hydrogen, such as alkyl, and all other $R^1$ and $R^2$ variables are hydrogen. Multiple branching is also envisioned wherein multiple instances of $R^1$ and/or $R^2$ are defined as an atom or group of atoms other than hydrogen (e.g., alkyl). It is preferred, however, that branched species include only a single branching point. In addition, it is preferred that the single branch point occurs at the carbon atom α to (or immediately adjacent to) the "branching carbon atom" in the ortho ester functionality.

Optionally, a spacer moiety can be located between the carbon chain and the suitable leaving group. Exemplary ortho esters comprising such a spacer moiety comprise the following structure:

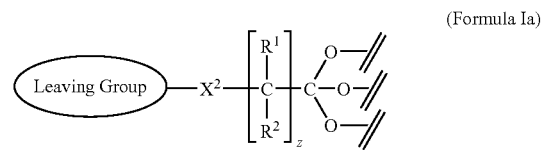 (Formula Ia)

wherein:
$X^2$ is a spacer moiety and

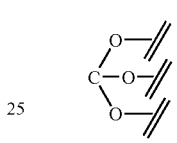, (z), each $R^1$, each $R^2$, and are as previously defined.

The optional spacer moiety (i.e., $X^2$) in the ortho ester comprising a suitable leaving group is any atom or series of atoms separating the carbon chain of (z) atoms from the leaving group. Depending on the actual atom or atoms that make up this spacer moiety, the spacer moiety can be hydrolytically stable or hydrolytically unstable. Whether any specific moiety is hydrolytically stable or unstable can be determined by one of ordinary skill in the art or determined experimentally using routine experimentation. This optional spacer moiety $X^2$ can be selected from the spacer moieties identified below with respect to X. In those instances where $X^2$ appears within the same structure defined as comprising an X or $X^1$, $X^2$ can be the same or different.

It should be stressed that although the ortho ester comprising a suitable leaving group comprises a carbon chain of (z) atoms, the presence of the carbon chain is not necessary to provide a carboxylic acid. Consequently, when a water-soluble polymer bearing a terminal carboxylic acid other than an alkanoic acid (e.g., a propanoic acid, butanoic acid, and so forth) is desired, the carbon chain is omitted and replaced by, for example, a spacer moiety or other group of atoms.

The ortho ester having a suitable leaving group can be prepared synthetically. For example, acyclic ortho esters can be prepared by obtaining an imino ester (also referred to as an "alkyl imidate") through, for example, a Pinner reaction. In this approach, an imino ester is formed via the addition of anhydrous hydrogen chloride gas to a mixture of a nitrile and an alcohol. Subsequent treatment of the imino ester with an alcohol yields the corresponding ortho ester. See, for example, Voss et al. (1983) *Helv. Chim. Acta.* 66:2294.

Cyclic ortho esters can be prepared via conversion of a hydroxyalkyloxetane to the corresponding carboxylic ester, which, following rearrangement, yields a bridged ortho ester. These and other approaches for preparing cyclic ortho esters are described in the literature. See, for example: Corey et al. (1983) *Tetrahedron Lett.* 24(50):5571-5574; Wipf et al. (1999) *Pure Appl. Chem.* 71(3):415-421; and Greene et al. PROTECTIVE GROUPS IN ORGANIC SYNTHESIS, 3rd ed., pp. 437-441, John Wiley & Sons, New York, N.Y. (1999). The suitable leaving group is introduced in the ortho ester by including the leaving group in the reactant prior to formation of the ortho ester or by adding it subsequent to the formation of the ortho ester.

In some cases, the ortho ester comprising a suitable leaving group is available commercially. For example, one commercially available ortho ester is trimethyl 4-bromoorthobutyrate available from Sigma-Aldrich Corporation of St. Louis, Mo.

The Water-Soluble Polymer Having at Least One Hydroxyl or Thiol Group

Any water-soluble polymer having at least one hydroxyl or thiol group (to provide, for example, a water-soluble polymer having at least one alkoxide ion or thiolate ion, respectively) can be used in accordance with the invention and the invention is not limited in this regard. Although water-soluble polymers bearing only a single hydroxyl or thiol can be used, polymers bearing two, three, four, five, six, seven, eight, nine, ten, eleven, twelve or more hydroxyl and/or thiol moieties can be used. Advantageously, as the number of hydroxyl or thiol moieties on the water-polymer segment increases, the number of available sites for providing carboxylic acid moieties increases. Nonlimiting examples of the upper limit of the number of hydroxyl and/or thiol moieties associated with the water-soluble polymer segment include 500, 100, 80 and 40.

The water-soluble polymer segment is preferably, although not necessarily, a poly(ethylene glycol) or "PEG" or a derivative thereof. It should be understood, however, that related polymers are also suited for use in the practice of this invention and that the use of the term "PEG" or "poly(ethylene glycol)" is intended to be inclusive and not exclusive in this respect. Consequently, the term "PEG" includes poly(ethylene glycol) in any of its linear, branched or multi-arm forms, including alkoxy PEG, bifunctional PEG, forked PEG, branched PEG, pendant PEG, or PEG with degradable linkages therein, to be more fully described below.

In one form useful in the present invention, free or non-bound PEG is a linear polymer terminated at each end with hydroxyl groups:

HO—CH$_2$CH$_2$O—(CH$_2$CH$_2$O)$_{m'}$—CH$_2$CH$_2$—OH (m') typically ranges from zero to about 4,000, preferably about 20 to about 1,000.

The above polymer, alpha-,omega-dihydroxylpoly(ethylene glycol), can be represented in brief form as HO-PEG-OH where it is understood that the -PEG- symbol can represent the following structural unit:

—CH$_2$CH$_2$O—(CH$_2$CH$_2$O)$_{m'}$—CH$_2$CH$_2$— where (m') is as defined as above.

Another type of PEG useful in the present invention is methoxy-PEG-OH, or mPEG in brief, in which one terminus is the relatively inert methoxy group, while the other terminus is a hydroxyl group. The structure of mPEG is given below.

CH$_3$O—CH$_2$CH$_2$O—(CH$_2$CH$_2$O)$_{m'}$—CH$_2$CH$_2$—OH where (m') is as described above.

Multi-armed or branched PEG molecules, such as those described in U.S. Pat. No. 5,932,462, can also be used as the PEG polymer. For example, PEG can have the structure:

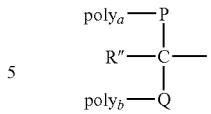

wherein:
poly$_a$ and poly$_b$ are PEG backbones (either the same or different), such as methoxy poly(ethylene glycol);
R" is a nonreactive moiety, such as H, methyl or a PEG backbone; and
P and Q are nonreactive linkages. In a preferred embodiment, the branched PEG polymer is methoxy poly(ethylene glycol) disubstituted lysine.

In addition, the PEG can comprise a forked PEG. An example of a forked PEG is represented by the following structure:

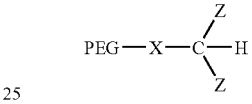

wherein: X is a spacer moiety and each Z is an activated terminal group linked to CH by a chain of atoms of defined length. International Application No. PCT/US99/05333, discloses various forked PEG structures capable of use in the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

-PEG-CO$_2$-PEG-+H$_2$O→-PEG-CO$_2$H+HO-PEG-

Other hydrolytically degradable linkages, useful as a degradable linkage within a polymer backbone, include carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Many other polymers are also suitable for the invention. Polymers that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), such as described in U.S. Pat. No. 5,629,384, and copolymers, terpolymers, and mixtures thereof. These polymers may be linear, or may be in any of the above-described forms (e.g., branched, forked, and the like).

Although the nominal average molecular weight of the water-soluble polymer can vary, the nominal average molecular weight will typically be in one or more of the following ranges: about 100 Daltons to about 100,000 Daltons; from about 500 Daltons to about 80,000 Daltons; from about 1,000 Daltons to about 50,000 Daltons; from about 2,000 Daltons to about 25,000 Daltons; from about 5,000 Daltons to about 20,000 Daltons. Exemplary nominal average molecular weights for the water-soluble polymer segment include about 1,000 Daltons, about 5,000 Daltons, about 10,000 Daltons, about 15,000 Daltons, about 20,000 Daltons, about 25,000 Daltons, and about 30,000 Daltons.

The PEG and other water-soluble polymers as described herein are typically considered to be biocompatible and non-immunogenic. With respect to biocompatibility, a substance is considered biocompatible if the beneficial effects associated with use of the substance alone or with another substance (e.g., active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician. It is particularly preferred that the polymers described herein as well as conjugates of active agents and the water-soluble polymers and segments described herein are biocompatible and non-immunogenic.

Those of ordinary skill in the art will recognize that the foregoing discussion concerning substantially water-soluble polymers is by no means exhaustive and is merely illustrative, and that all polymeric materials having the qualities described above are contemplated. As used herein, the "term water-soluble polymer" generally refers to an entire molecule, which can comprise functional groups such as hydroxyl groups, thiol groups, ortho ester functionalities and so forth. The term water-soluble polymer segment is generally reserved for use in discussing specific molecular structures wherein a polymer or portion thereof is but one part of the overall molecular structure.

An example of a preferred water-soluble polymer bearing a hydroxyl or thiol moiety comprises the following structure:

POLY-(X)$_a$—YH (Formula II)

wherein POLY is a water-soluble polymer segment;

(a) is zero or one;

X, when present, is a spacer moiety; and

Y is O or S.

Recognizing certain instances wherein a water-soluble polymer segment (i.e., a "POLY") is defined as containing a hydroxyl or thiol moiety (e.g., $CH_3O$—$(CH_2CH_2O)_m$—H or $CH_3O$—$(CH_2CH_2O)_m$—$(CH_2CH_2S)$—H, respectively), the "—YH" moiety of Formula II is understood to represent the hydroxyl or thiol moiety of "POLY" and not the irrational interpretation of, for example, "$CH_3O$—$(CH_2CH_2O)_m$—H—YH." Alternatively, $CH_3O$—$(CH_2CH_2O)_m$—H, for example, is encompassed by Formula II when POLY is defined as "$CH_3O$—$(CH_2CH_2O)_m$—," (a) is one, X is "—$CH_2CH_2$—" and Y is "—O—". Thus, given the possibility that there can be more than a single way for any individual molecule to be encompassed by a given formula, due consideration must be given in order to determine whether a molecule in question is or is not encompassed by a given formula.

A particular preferred water-soluble segment bearing a single hydroxyl group comprises the following structure:

$R^5$—O—$(CH_2CH_2O)_m$—H wherein:

(m) is from 2 to 4000; and $R^5$ is an end-capping group such as H or an organic radical selected from the group consisting of alkyl, substituted alkyl, alkenyl, substituted alkenyl, alkynyl, substituted alkynyl, aryl, and substituted aryl. It is especially preferred that $R^5$ is a lower alkyl such as methyl, although benzyl and other end-capping groups known to those of skill in the art can also be used.

For purposes of the present disclosure, however, a series of atoms is not a spacer moiety when the series of atoms is immediately adjacent to a polymer and the series of atoms is but another monomer such that the proposed spacer moiety would represent a mere extension of the polymer chain. For example, given the partial structure "POLY-X—," and POLY is defined as "$CH_3O(CH_2CH_2O)_m$—" wherein (m) is 2 to 4000 and X is defined as a spacer moiety, the spacer moiety cannot be defined as "—$CH_2CH_2O$—" since such a definition would merely represent an extension of the polymer. In such a case, however, an acceptable spacer moiety could be defined as "—$CH_2CH_2$—."

Exemplary spacer moieties include, but are not limited to, —C(O)—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—, —$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—C(O)—NH—$CH_2$—$CH_2$—, —$CH_2$—$CH_2$—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—

NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes.

In the present context of an amino acid being included in the structures provided herein, it should be remembered that the amino acid is connected to the rest of the structure via one, two, three or more sites. For example, a spacer moiety can result when an amino acid is attached to the rest of the molecule via two covalent attachments. In addition, a branching structure can result when an amino acid is attached to the rest of the molecule via three sites. Thus, the amino acid structure necessarily changes somewhat due to the presence of one or more covalent attachments (e.g., removal of a hydrogen atom from the amino acid in order to accommodate a covalent linkage). Consequently, reference to an "amino acid" therefore includes the amino acid containing one or more linkages to other atoms. The amino acid can be selected from the group consisting of alanine, arginine, asparagines, aspartic acid, cysteine, glutamic acid, glutamine, glycine, histidine, isoleucine, leucine, lysine, methionine, phenylalanine, proline, serine, threonine, tryptophan, tyrosine, and valine. Both the D and L forms of the amino acids are contemplated.

The Ortho Ester of a Water-Soluble Polymer

The present invention provides for water-soluble polymers comprising an ortho ester functionality. As described above, both acyclic and cyclic forms of the ortho ester functionality are included. Exemplary cyclic ortho esters of water-soluble polymers of the invention are shown below:

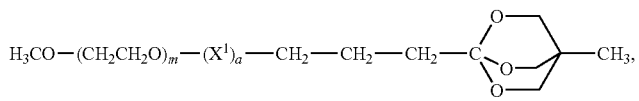

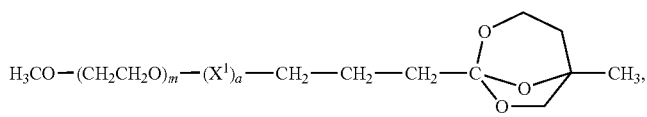

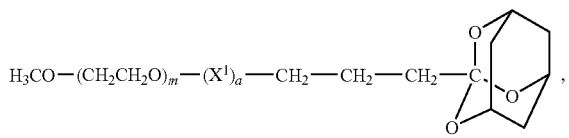

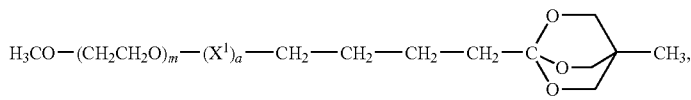

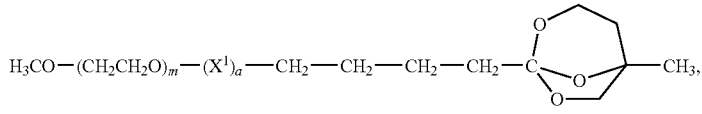

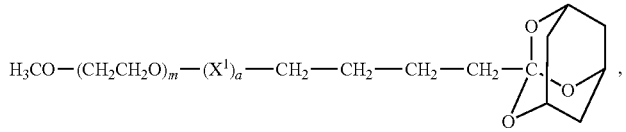

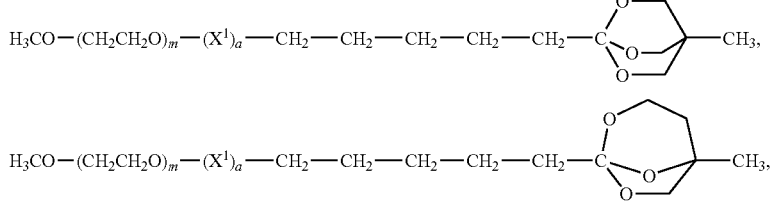

-continued
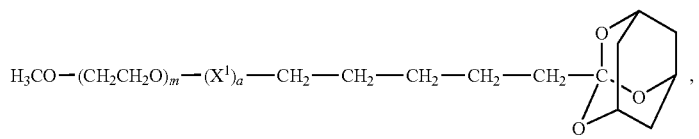
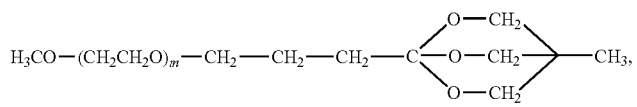
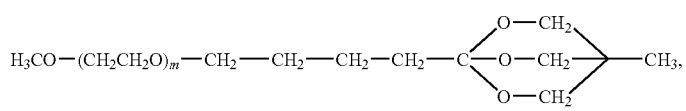
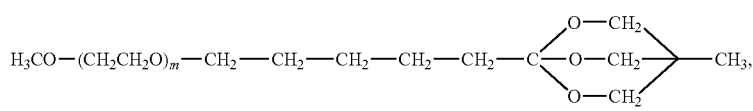
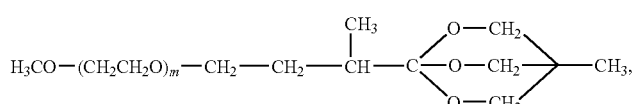
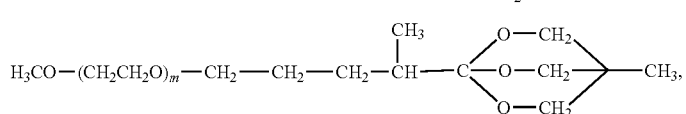
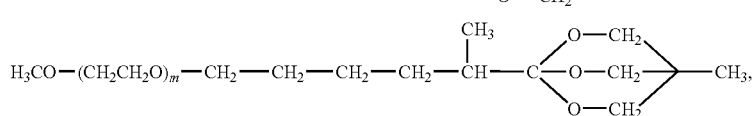
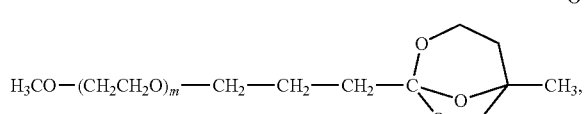
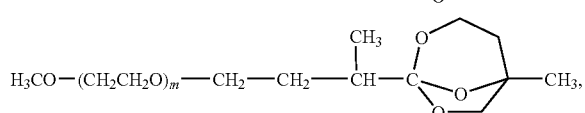
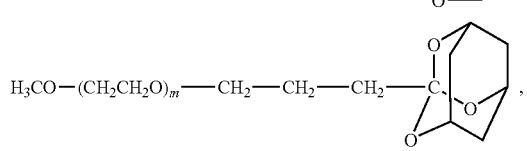
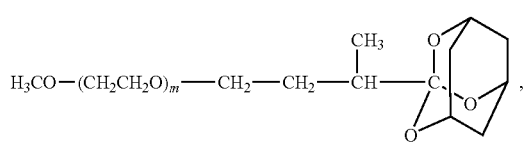
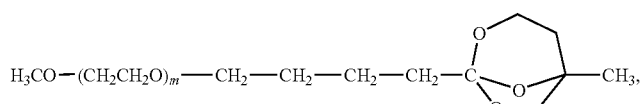
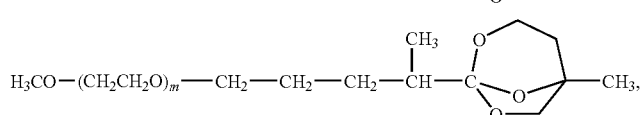
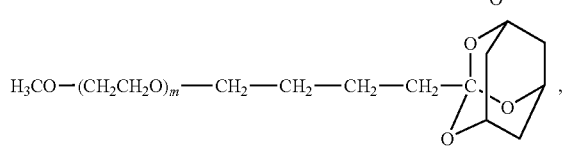

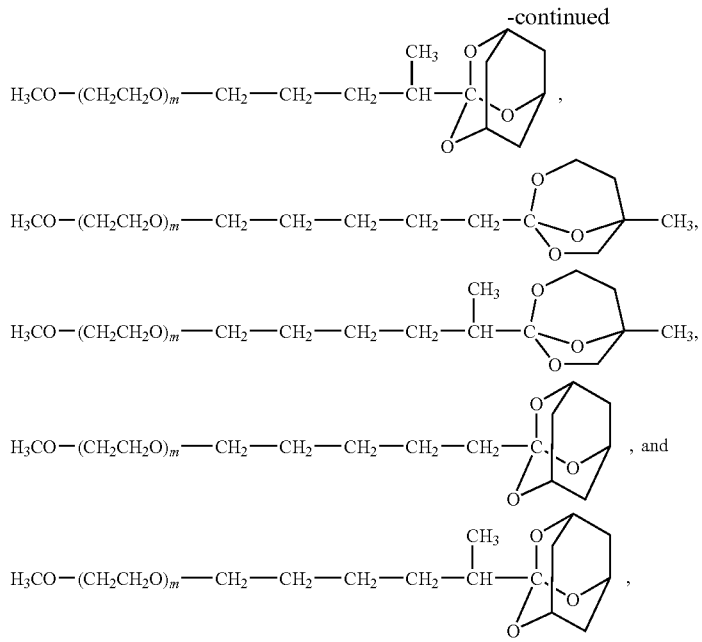

wherein (m) is 2 to 4000, (a) is zero or one, and $X^1$, when present, is a spacer moiety. Of course, other water-soluble polymers comprising an ortho ester moiety are also possible and in accordance with the present invention.

The Water-Soluble Polymer Bearing a Terminal Carboxylic Acid or Ester Thereof

In accordance with the present methods, any number of polymers bearing a terminal carboxylic acid or ester thereof can be prepared and the invention is not limited in this regard. Consequently, the invention includes carboxylic acids, such as alkanoic acids, and the corresponding esters of a polymer formed by a method as provided herein.

With respect to alkanoic acids then, the invention provides for alkanoic acids comprising the following structure:

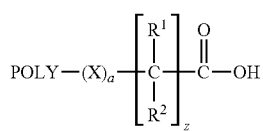

(Formula V)

wherein:
POLY is a water-soluble polymer segment;
(a) is either zero or one;
X, when present, is a spacer moiety;
(z) is an integer from 1 to 24;
$R^1$, in each occurrence, is independently H or an organic radical selected from the group consisting of alkyl, substituted alkyl, alkenyl, substituted alkenyl, alkynyl, substituted alkynyl, aryl, and substituted aryl; and
$R^2$, in each occurrence, is independently H or an organic radical selected from the group consisting of alkyl, substituted alkyl, alkenyl, substituted alkenyl, alkynyl, substituted alkynyl, aryl, and substituted aryl.

In addition, esters of the water-soluble polymer bearing a terminal carboxylic acid are provided. For example, the corresponding esters of the carboxylic acids of Formula V preferably have the following structure:

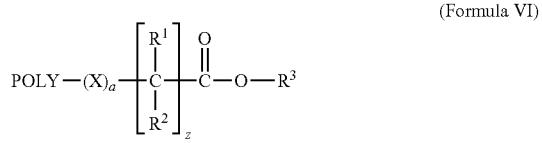

(Formula VI)

wherein POLY, (a), X, when present, (z), each $R^1$, and each $R^2$ are as previously defined, and $R^3$ is an organic radical selected from the group consisting of alkyl, substituted alkyl, alkenyl, substituted alkenyl, alkynyl, substituted alkynyl, aryl, and substituted aryl. In order to refer to polymers bearing a terminal carboxylic acid or ester thereof, $R^3$ can conveniently be defined as H (thereby referring to the acid) or an organic radical selected from the group consisting of alkyl, substituted alkyl, alkenyl, substituted alkenyl, alkynyl, substituted alkynyl, aryl, and substituted aryl (thereby referring to a corresponding ester). The carboxylic acids and esters provided herein include sulfur-substituted versions, e.g., —C(O)—S—$R^3$, as well.

For any given carboxylic acid, the corresponding ester can be formed using conventional techniques. For example, the water-soluble polymer bearing a terminal carboxylic acid can undergo acid-catalyzed condensation with an alcohol, thereby providing the corresponding ester. One approach to accomplish this is to use the method commonly referred to as a Fischer esterification reaction. Other techniques for forming a desired ester are known by those of ordinary skill in the art.

In addition, the water-soluble polymer bearing a terminal carboxylic acid can be modified to form useful reactive derivatives of alkanoic acids using methodology known in the art. For example, the carboxylic acid can be further derivatized to form acyl halides, acyl pseudohalides, such as acyl cyanide, acyl isocyanate, and acyl azide, neutral salts, such as alkali metal or alkaline-earth metal salts (e.g. calcium, sodium, and barium salts), esters, anhydrides, amides, imides, hydrazides, and the like. In a preferred embodiment, the carboxylic acid is esterified to form an N-succinimidyl ester, o-, m-, or p-nitrophenyl ester, 1-benzotriazolyl ester, imidazolyl ester, or N-sulfosuccinimidyl ester. For example, the carboxylic acid can be converted into the corresponding N-succinimidyl ester by reacting the carboxylic acid with dicyclohexyl carbodiimide (DCC) or diisopropyl carbodiimide (DIC) in the presence of a base.

Particularly preferred polymers bearing a terminal carboxylic acid moiety, however, are those wherein the carboxylic acid moiety forms part of an alkanoic acid. In this respect, carbon chains of four or more carbon atoms (including the carbonyl carbon) that terminate in a carboxylic acid or non-aromatic ester are preferred. It is preferred that the water-soluble polymer segment is covalently attached through one or more atoms to the distal carbon (with respect to the carbonyl carbon) in the carbon chain that is at least four carbon atoms. Moreover, when the water-soluble polymer segment is covalently attached through only one atom, the one atom is not O or S. Such polymers can be structurally defined as follows:

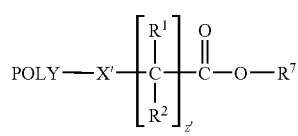
(Formula VIa)

wherein:

POLY is a water-soluble polymer segment;

X' is a spacer moiety with the proviso that when the spacer moiety is only one atom, the one atom is not O or S;

(z') is an integer from 3 to 21;

$R^1$, in each occurrence, is independently H or an organic radical selected from the group consisting of alkyl, substituted alkyl, alkenyl, substituted alkenyl, alkynyl, substituted alkynyl, aryl, and substituted aryl;

$R^2$, in each occurrence, is independently H or an organic radical selected from the group consisting of alkyl, substituted alkyl, alkenyl, substituted alkenyl, alkynyl, substituted alkynyl, aryl, and substituted aryl; and $R^7$ is H or an organic radical selected from the group consisting of alkyl, substituted alkyl, alkenyl, substituted alkenyl, alkynyl, and substituted alkynyl.

Preferably, (z') is three, four, or five. When (z') is equal to three, the polymer of Formula VIa is comprised of the following structure:

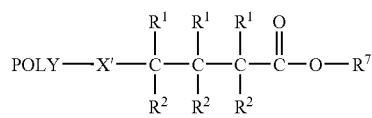
(Formula VIb)

wherein POLY, X', each $R^1$, each $R^2$ and $R^7$ are as previously defined.

When (z') is equal to four, the polymer of Formula VIa is comprised of the following structure

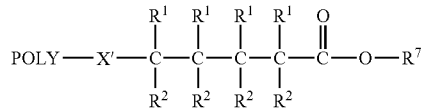
(Formula VIc)

wherein POLY, X', each $R^1$, each $R^2$ and $R^7$ are as previously defined.

When (z') is equal to five, the polymer of Formula VIa is comprised of the following structure:

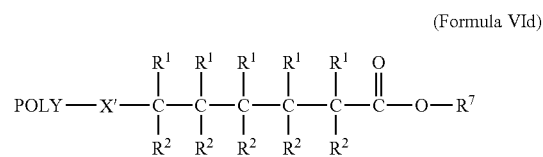
(Formula VId)

wherein POLY, X', each $R^1$, each $R^2$ and $R^7$ are as previously defined.

In each of these cases, $R^7$ is hydrogen when the carboxylic acid is desired. With respect to $R^1$ and $R^2$, in some instances, each $R^1$ and $R^2$ is hydrogen. In other instances, however, the $R^1$ attached to the carbon α to the carbonyl carbon is alkyl (e.g., methyl, ethyl, n-propyl, isopropyl, n-butyl, sec-butyl, isobutyl, and tert-butyl) and all other $R^1$ variables are H and all $R^2$ variables are hydrogen. As is known by those of ordinary skill in the art, the "carbon α to the carbonyl" indicates the carbon atom directly attached to the carbonyl carbon. For illustrative purposes, the "carbon α to the carbonyl carbon" as well as the "carbonyl carbon" are labeled in the following structure:

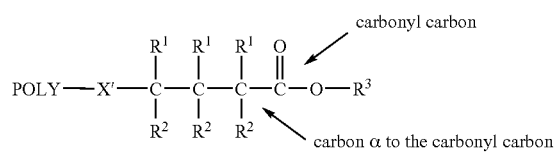

Other arrangements are also envisioned wherein $R^1$ attached to the carbon atom β, γ or δ, to the carbonyl carbon is an organic radical. In addition, combinations in which two or more $R^1$ substituents are defined as an organic radical are possible. These same substitutions apply to the corresponding ortho ester polymers and reagents.

When the carbon α to the carbonyl carbon bears an organic radical (e.g., methyl), the resulting polymer may comprise a chiral center. Specific chirality, however, is not explicitly illustrated herein with respect to any compound or structure comprising one or more chiral centers and the invention is intended to encompass both the isomerically pure forms of the compound or structure as well as diastereomeric mixtures, including a racemic mixture, thereof.

X' is the same as X, as defined above, with the exception that X' is not O or S.

The carboxylic acids as provided herein may also be defined through the following formula:

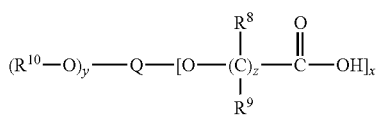

wherein:

$R^{10}$ is H or an organic radical selected from the group consisting of alkyl, substituted alkyl, alkenyl, substituted alkenyl, alkynyl, substituted alkynyl, aryl, and substituted aryl;

Q is a residue of a polyhydric alcohol having x+y hydroxyl groups;

$R^8$, in each occurrence, is independently H or an organic radical selected from the group consisting of alkyl, substituted alkyl, alkenyl, substituted alkenyl, alkynyl, substituted alkynyl, aryl, and substituted aryl;

$R^9$, in each occurrence, is independently H or an organic radical selected from the group consisting of alkyl, substituted alkyl, alkenyl, substituted alkenyl, alkynyl, substituted alkynyl, aryl, and substituted aryl;

(x) is 1 to 20, preferably 2, 3, 4, 5, or 6;

(y) is 1 to 20; and (z) is 1 to 24, preferably from 4 to 20.

Representative Q moieties include the following: propylene glycol, glcerine, sorbitol, pentaerythritol, dipentaerythritol, dihydroxycyclohexane, glucose, galactose, mannose, fructose, mannose, lactose, sucrose, amylose, as well as other sugars.

An example preferred polymer bearing two terminal carboxylic acid moieties (a "forked" structure) comprises the following:

preferred to minimize the amount moisture associated with the storage conditions to reduce potentially damaging reactions associated with water. Moreover, it is preferred to keep the storage conditions dark in order to prevent certain degradative processes that involve light. Thus, preferred storage conditions include one or more of the following: storage under dry argon or another dry inert gas; storage at temperatures below about −15° C.; storage in the absence of light; and storage with a suitable amount (e.g., about 50-500 parts per million) of an antioxidant such as BHT.

Conjugation Method

The above-described polymers bearing a terminal carboxylic acid, optionally in an activated form, are useful for conjugation to biologically active agents or surfaces comprising at least one group suitable for reaction with a carboxylic acid or the optional activated form. Exemplary groups suitable for reaction with a carboxylic acid include amino groups (e.g., primary amines), hydrazines, hydrazides, and alcohols. Often, the polymer bearing a terminal carboxylic acid moiety can be conjugated directly to the active agent or surface. Sometimes, however, it is necessary to form an "activated" version of the carboxylic acid in order to enhance reactivity to the biologically active agent or surface. Methods for activating carboxylic acids are known in the art and include, for example, dissolving the water-soluble polymer bearing a terminal carboxylic acid in methylene chloride and subsequently adding N-hydroxysuccinimide and N,N-dicyclohexylcarbodiimide (DCC) to form an activated N-succinimidyl ester version of the carboxylic acid. Other approaches for activating a carboxylic acid are known to those of ordinary skill in the art.

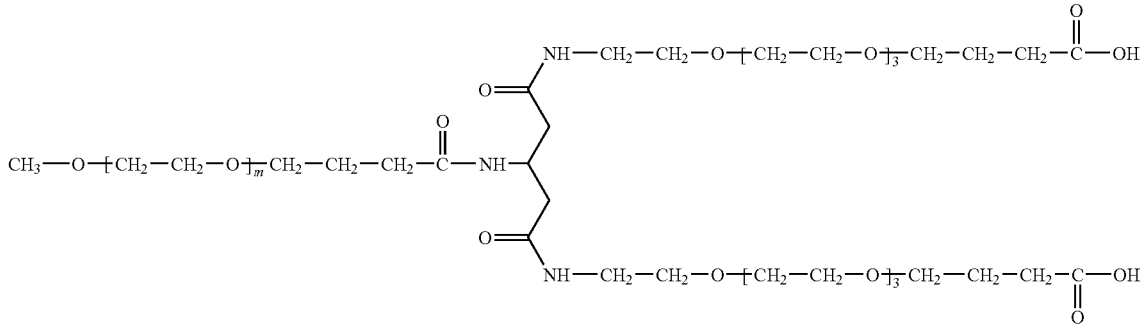

wherein (m) is from 2 to 4000. Preferably, however, the weight average molecular weight for the water-soluble polymer segment is from about 5,000 Daltons to about 40,000 Daltons, more preferably from about 20,000 Daltons to about 30,000 Daltons, with a molecular weight of about 20,000 Daltons being most preferred.

Storage Conditions Generally

The polymers bearing a terminal carboxylic acid or ester thereof, as well as any intermediates in their formation (e.g., ortho esters of water-soluble polymers), can be stored under an inert atmosphere, such as under argon or under nitrogen. In this way, potentially degradative processes associated with, for example, atmospheric oxygen, are avoided or reduced entirely. In some cases, to avoid oxidative degradation, antioxidants, such as butylated hydroxyl toluene (BHT), can be added to the final product prior to storage. In addition, it is Typically, the water-soluble polymer bearing the carboxylic acid or ester thereof is added to the active agent or surface at an equimolar amount (with respect to the desired number of groups suitable for reaction with the carboxylic acid or ester thereof) or at a molar excess. For example, the polymer can be added to the target active agent at a molar ratio of about 1:1 (polymer:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

Characterization/Separation

With respect to polymer-active agent conjugates, the conjugates can be purified to obtain/isolate different conjugated species. Alternatively, and more preferably for lower molecular weight (e.g., less than about 20 kiloDaltons, more preferably less than about 10 kiloDaltons) polymers, the product mixture can be purified to obtain the distribution of water-soluble polymer segments per active agent. For example, the product mixture can be purified to obtain an average of anywhere from one to five PEGs per active agent (e.g., protein), typically an average of about 3 PEGs per active agent (e.g., protein). The strategy for purification of the final conjugate reaction mixture will depend upon a number of factors, including, for example, the molecular weight of the polymer employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymer-to-active agent ratios (e.g., 1-mer, 2-mer, 3-mer, and so forth, wherein "1-mer" indicates 1 polymer to active agent, "2-mer" indicates two polymers to active agent, and so on) on the basis of their differing molecular weights (where the difference corresponds essentially to the average molecular weight of the water-soluble polymer segments). For example, in an exemplary reaction where a 100 kDa protein is randomly conjugated to a PEG alkanoic acid having a molecular weight of about 20 kDa, the resulting reaction mixture will likely contain unmodified protein (MW 100 kDa), mono-pegylated protein (MW 120 kDa), di-pegylated protein (MW 140 kDa), and so forth. While this approach can be used to separate PEG and other polymer conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content [Sims et al. (1980) *Anal. Biochem,* 107:60-63], and (iv) sodium dodecyl sulfphate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

Storage Conditions of Polymer-Active Agent Conjugates

Following conjugation, and optionally additional separation steps, the conjugate mixture may be concentrated, sterile filtered, and stored at low a temperature, typically from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized powder is absent residual buffer. Alternatively, a buffer exchange step may be used using a formulation buffer, so that the lyophilized conjugate is in a form suitable for reconstitution into a formulation buffer and ultimately for administration to a mammal.

Active Agents and Surfaces

The water-soluble polymers bearing a carboxylic acid or ester thereof presented herein, can be attached, either covalently or non-covalently, to a number of entities including films, chemical separation and purification surfaces, solid supports, metal surfaces such as gold, titanium, tantalum, niobium, aluminum, steel, and their oxides, silicon oxide, macromolecules (e.g., proteins, polypeptides, and so forth), and small molecules. Additionally, the polymers can also be used in biochemical sensors, bioelectronic switches, and gates. The polymers can also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in coupling to a polymer as presented herein may be any one or more of the following. Suitable agents can be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

Specific examples of active agents suitable for covalent attachment include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, trastuzumab (herceptin), and adalimumab.

Additional agents suitable for covalent attachment include, but are not limited to, adefovir, alosetron, amifostine, amiodarone, aminocaproic acid, aminohippurate sodium, aminoglutethimide, aminolevulinic acid, aminosalicylic acid, amsacrine, anagrelide, anastrozole, aripiprazole, asparaginase, anthracylines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, dutasteride, epirubicin, estramustine, etoposide, exemestane, ezetimibe, fexofenadine, fludarabine, fludrocortisone, fluorouracil, fluoxymesterone, flutamide, fondaparinux, fulvestrant, gamma-hydroxybutyrate, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, nitisinone, octreotide, oxaliplatin, pamidronate, pentostatin, pilcamycin, porfimer, prednisone, procarbazine, prochlorperazine, ondansetron, oxaliplatin, raltitrexed, sirolimus, streptozocin, tacrolimus, pimecrolimus, tamoxifen, tegaserod, temozolomide, teniposide, testosterone, tetrahydrocannabinol, thalidomide, thioguanine, thiotepa, topotecan, treprostinil, tretinoin, valdecoxib, celecoxib, rofecoxib, valrubicin, vinblastine, vincristine, vindesine, vinorelbine, voriconazole, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicilinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred small molecules for coupling to a polymer as described herein are those having at least one naturally occurring amino group. Preferred molecules such as these include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymer as described herein include EPO, IFN-α, IFN-β, consensus IFN, Factor VIII, Factor IX, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof.

Pharmaceutical Compositons

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

Methods of Administering

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

It is to be understood that while the invention has been described in conjunction with the preferred specific embodiments thereof, that the foregoing description as well as the experimental that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are hereby incorporated by reference in their entireties.

EXPERIMENTAL

EXAMPLES

The practice of the invention will employ, unless otherwise indicated, conventional techniques of organic synthesis and the like, which are understood by one of ordinary skill in the art and are explained in the literature. In the following examples, efforts have been made to ensure accuracy with respect to numbers used (e.g., amounts, temperatures, and so forth), but some experimental error and deviation should be accounted for. Unless otherwise indicated, temperature is in degrees Celsius and pressure is at or near atmospheric pressure at sea level. All reagents were obtained commercially unless otherwise indicated. All generated NMR was obtained from a 300 or 400 MHz NMR spectrometer manufactured by Bruker (Billerica, Mass.). Reference to an "OBO ortho ester" corresponds to esters comprising the 4-methyl-2,6,7-trioxabicyclo[2.2.2]octanyl.

Example 1

Formation of 4-Bromobutyrate ester of 3-methyl-3-hydroxymethyloxetane (MW=251.12)

3-Methyl-3-hydroxymethyloxetane (10.2 g, 0.1 mole) (Sigma-Aldrich Corporation, St. Louis, Mo.) was dissolved in anhydrous dichloromethane (200 ml). Pyridine (9.8 ml, 0.12 moles) was then added to the solution. Thereafter, the solution was cooled to 0° C. and 4-bromobutyryl chloride (18.5 g, 0.1 mole) (Sigma-Aldrich Corporation, St. Louis, Mo.) dissolved in anhydrous dichloromethane (50 ml) was added dropwise over 20 minutes. The mixture was stirred overnight under argon atmosphere. Next, the reaction mixture was washed with water and dried with anhydrous magnesium sulfate. The solvent was then distilled off under reduced pressure. Yield 23.6 g. NMR ($d_6$-DMSO): 1.26 ppm (s, 3H), 2.07 ppm (m, 2H), 2.51 ppm (t, 2H), 3.56 ppm (t, 2H), 4.14 ppm (s, 2H), 4.24 ppm (d, 2H), 4.38 ppm (d, 2H).

Example 2

Formation of 1-(3-Bromopropyl)-4-methyl-2,6,7-trioxabicyclo[2,2,2]octane (MW=251.12)

The product of Example 1 (crude 4-bromobutyrate ester of 3-methyl-3-hydroxymethyloxetane, 20.1 g, 0.08 moles) was dissolved in anhydrous dichloromethane (100 ml), the solution was cooled to 0° C. and boron trifluoride diethyl etherate (2.5 ml, 0.022 moles) was added. The mixture was then stirred for four hours at 0° C. Triethylamine (12 ml) was added, the mixture was stirred for 15 minutes, and the solvent was distilled off under reduced pressure. The crude product was dissolved in ethyl ether (180 ml) and the solution was then filtered to remove the solid impurities. Next, ether was distilled off and the product was distilled under reduced pressure (kugelrohr, 110-115° C., 0.05 mm Hg). Yield 15.0 g. NMR ($d_6$-DMSO): 0.74 ppm (s, 3H), 1.68 ppm (m, 2H), 1.88 ppm (m, 2H), 3.52 ppm (t, 2H), 3.81 ppm(s, 6H).

Example 3

Synthesis of a PEG-Butanoic Acid Precursor Useful in a Polymerization Reaction A mixture of anhydrous ethylene glycol (120 g, 1.93 moles), 1.0M solution of potassium tert-butoxide in tert-butanol (70 ml, 0.070 moles), and the product of Example 2 [1-(3-bromopropyl)-4-methyl-2,6,7-trioxabicyclo[2,2,2]octane (15 g, 0.060 moles)] was stirred overnight at 70° C. under an argon atmosphere. After cooling to room temperature, the reaction mixture was added to 600 ml of distilled water. The product was three-times extracted with dichloromethane (150 ml, 125 ml, and 125 ml). The combined extracts were dried with anhydrous magnesium sulfate and the solvent was distilled off under reduced pressure. The product (Compound 1) was then subjected to vacuum distillation (kugelrohr, t=120-130° C., 0.05 mm Hg). Yield 6.2 g. NMR ($d_6$-DMSO): 0.74 ppm (s, 3H), 1.59 ppm (m, 4H), 3.34 ppm (m, 4H), 3.45 ppm (t, 2H), 3.80 ppm(s, 6H), 4.54 ppm (t, 1H).

Schematically, the reaction can be represented as follows:

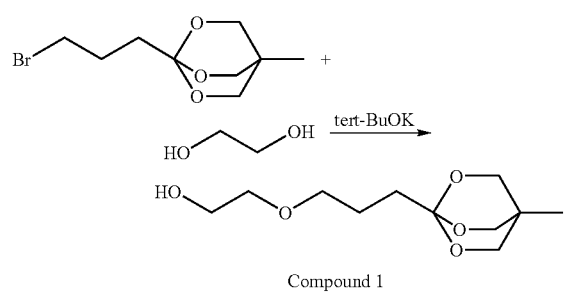

Compound 1

Example 4

Synthesis of a PEG-Propanoic Acid Precursor Useful in a Polymerization Reaction Tert-butyl acrylate (130 g, 1.01 mole) was added dropwise over 3 hours to a mixture of anhydrous ethylene glycol (62 g, 1.0 mole), tetrabutylammonium bromide (9.6 g) and KOH (powder, 2.2 g), and stirred overnight at room temperature under an argon atmosphere. The volatile products were distilled off under reduced pressure (rotoevaporator, 60° C.) and the mixture was dissolved in 250 ml dichloromethane. The solution was washed with 250 ml of distilled water, dried with anhydrous magnesium sulfate, and the solvent was distilled off under reduced pressure. The product (Compound 2) was then subjected to vacuum distillation (kugelrohr, t=95-100° C., 0.05 mm Hg). Yield 36.6 g. NMR ($d_6$-DMSO): 1.40 ppm (s, 9H), 2.42 ppm (t, 2H), 3.39 ppm (m, 2H), 3.46 ppm (m, 2H), 3.59 ppm(s, 2H), 4.55 ppm (t, 1H).

Schematically, the reaction can be represented as follows:

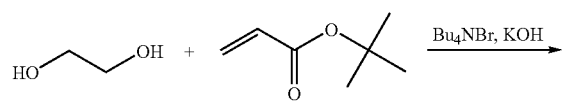

-continued

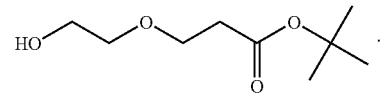

Compound 2

A mixture of Compound 2 (36.6 g, 0.19 moles), pyridine (52 ml, 0.64 moles), acetic anhydride (52 ml, 0.55 moles) and dimethylaminopyridine (DMAP, 1.0 g) was stirred overnight at room temperature. The volatile products were then distilled off under reduced pressure (rotoevaporator, t=65° C.) and the product (Compound 3) was subjected to vacuum distillation (kugelrohr, 100-110° C., 0.05 mm Hg). Yield 40.9 g. NMR ($d_6$-DMSO): 1.40 ppm (s, 9H), 2.02 ppm (s, 3H), 2.42 ppm (t, 2H), 3.58 ppm (bm, 4H), 4.08 ppm (m, 2H).

Schematically, the reaction can be represented as follows:

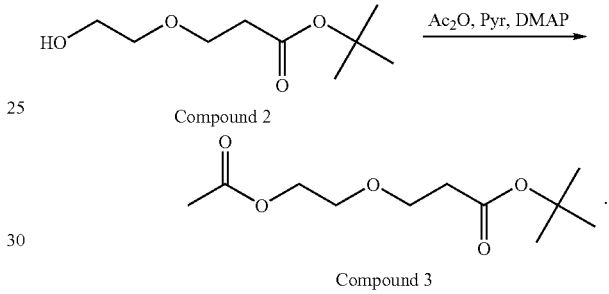

Compound 3

To compound 3 (30.0 g, 0.19 moles), trifluoroacetic acid (40 ml) was added and the solution was stirred for 1 hour at room temperature. The volatile products were then distilled off under reduced pressure (rotoevaporator, t=60° C.) and the product was dissolved in 400 ml dichloromethane. The solution was washed twice with 5% NaCl solution and dried with anhydrous magnesium sulfate and the solvent was distilled off under reduced pressure to provide Compound 4. Yield 19.1 g. NMR ($d_6$-DMSO): 2.01 ppm (s, 3H), 2.44 ppm (t, 2H), 3.57 ppm (m, 2H), 3.61 ppm (t, 2H) 4.09 ppm (m, 2H).

Schematically, the reaction can be represented as follows:

Compound 3

Compound 4

To a solution of compound 4 (19.1 g, 0.108 moles), 3-methyl-3-hydroxyoxetane (17.6 g, 0.172 moles), 1-hydroxybenzotriazole (HOBt, 1.6 g), and DMAP (3.6 g) in anhydrous dichloromethane (500 ml), along with 1,3-dicyclohexylcarbodiimide (DCC, 1.0M solution in dichloromethane, 114 ml, 0.114 moles) was added at 0° C., and the mixture was stirred overnight at room temperature. The mixture was then filtered to remove precipitated 1,3-dicyclohexylurea and the solution was washed with 250 ml of 5% H₃PO₄. Next, the dichloromethane was distilled off under reduced pressure (rotoevaporator) and the product (Compound 5) was subjected to vacuum distillation (kugelrohr, 125-135° C., 0.05 mm Hg). Yield 18.5 g. NMR (d₆-DMSO): 1.26 ppm (s, 3H), 2.00 ppm (s, 3H), 2.59 ppm (t, 2H), 3.57 ppm (m, 2H), 3.66 ppm (t, 2H), 4.08 ppm (m, 2H), 4.14 ppm (s, 2H), 4.23 ppm (d, 2H), 4.38 ppm (d, 2H).

Schematically, the reaction can be represented as follows:

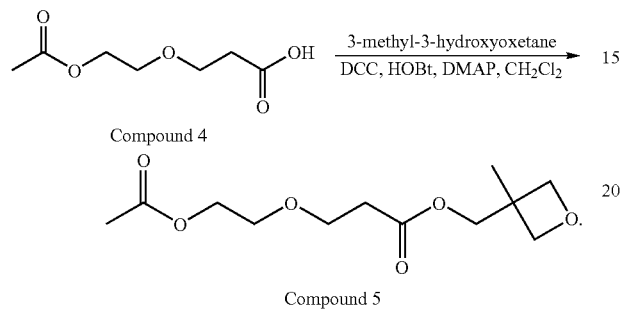

Compound 5 (15.0 g, 0.08 moles) was then dissolved in anhydrous dichloromethane (75 ml), the solution was cooled to 0° C. and boron trifluoride diethyl etherate (1.65 ml) was added. The mixture was then stirred for 3 hours at 0° C. Triethylamine (7.5 ml) was added, the mixture was stirred for 10 minutes, and the solvent was distilled off under reduced pressure. The crude product (Compound 6) was dissolved in ethyl ether (150 ml) and the solution was filtered to remove the solid impurities. The ether was then distilled off. Yield 12.9 g. NMR (d₆-DMSO): 0.74 ppm (s, 3H), 1.83 ppm (t, 2H), 2.00 ppm (s, 3H), 3.46 ppm (t, 2H), 3.52 ppm (m, 2H), 3.80 ppm (s, 2H), 3.52 ppm (t, 6H), 4.07 ppm (m, 2H).

Schematically, the reaction can be represented as follows:

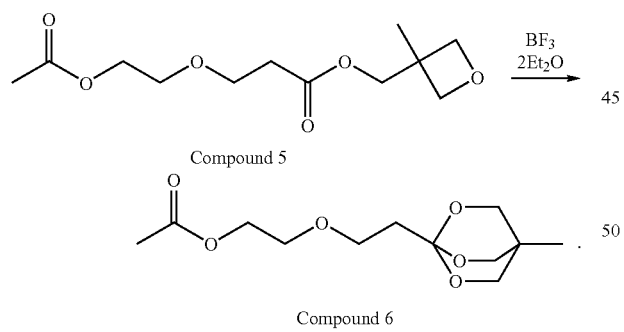

A mixture of compound 6 (12 g), ethyl alcohol (80 ml), and 50% aqueous solution of potassium hydroxide (8 g) was stirred for 40 minutes at room temperature. The solvent was then distilled off under reduced pressure (rotoevaporator). The crude product was dissolved in 400 ml dichloromethane and the solution was washed with 5% aqueous solution of sodium chloride. Next, the solution was dried with anhydrous MgSO₄ and the solvent was distilled off under reduced pressure (rotoevaporator) giving 8.0 g of colorless liquid product (Compound 7). NMR (d₆-DMSO): 0.74 ppm (s, 3H), 1.83 ppm (t, 2H), 3.35 ppm (m, 2H), 3.46 ppm (m, 4H), 3.80 ppm (s, 6H), 3.52 ppm (t, 6H), 4.54 ppm (t, 1H).

Schematically, the reaction can be represented as follows:

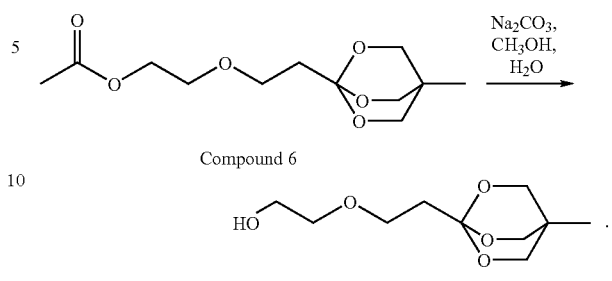

Example 5

Formation of PEG$_{(3,500\ Da)}$-α-hydroxy-ω-butanoic Acid, OBO Ortho Ester Using Compound 1 as the Initiator for Polymerization Compound 1 (0.564 g, 0.00243 moles), tetrahydrofuran (THF, 200 ml), and potassium naphthalene, 0.3 mol/1-tetrahydrofuran solution (10 ml, 0.00300 moles) were added to a glass reactor and stirred for 3 minutes in an argon atmosphere. Ethylene oxide (8.8 g, 0.20 moles) was added to this solution and the reaction mixture was stirred for 44 hours at room temperature. Next, the mixture was purged with argon and 0.1M phosphate buffer (pH=8, 100 ml) was added. The THF layer was separated and discarded. Naphthalene was removed from the solution by ethyl ether extraction. The product was then extracted with dichloromethane (3×50 ml). The extract was dried with anhydrous sodium sulfate and the solvent was distilled off under reduced pressure. Yield 7.2 g. NMR (d₆-DMSO): 0.73 ppm (s, —CH₃ of OBO, 3H), 1.57 ppm (m, —CH₂—CH₂—CO—, 4H), 3.51 ppm (s, PEG backbone), 3.80 ppm (s, CH₂ of OBO, 6H), 4.58 ppm (t, —OH, 1H).

Example 6

Formation of PEG$_{(3,500\ Da)}$-α-hydroxy-ω-butanoic Acid

The product of Example 5 (i.e., PEG$_{(3,500\ Da)}$-α-hydroxy-ω-butanoic acid, OBO ortho ester, 7.0 g) was dissolved in distilled water (100 ml). The pH of the solution was adjusted to 2 with 5% phosphoric acid and the solution was stirred for 15 minutes at room temperature. Next, the pH was readjusted to 12 by adding 1M sodium hydroxide and the solution was stirred for two hours while maintaining a pH equal to 12 by periodic addition of 1M sodium hydroxide. The pH was then adjusted to 3 with 5% phosphoric acid, after which the product was extracted with dichloromethane. The extract was dried with anhydrous magnesium sulfate and added to ethyl ether. The precipitated product was filtered off and dried under reduced pressure. Yield 6.6 g. NMR (d₆-DMSO): 1.72 ppm (q, CH₂—CH₂—COO—, 2H) 2.24 ppm (t, —CH₂—COO—, 2H), 3.51 ppm (s, PEG backbone), 4.58 ppm (t, —OH, 1H).

Example 7

Formation of mPEG$_{(3,500\ Da)}$-butanoic Acid, OBO Ortho Ester

A mixture of the product of Example 5 (i.e., PEG$_{(3,500\ Da)}$-α-hydroxy-ω-butanoic acid, OBO ortho ester, 7.0 g, 0.002 moles), toluene (100 ml), 1.0M solution of potassium tert-butoxide in tert-butanol (10 ml, 0.01 moles), and methyl p-toluenesulfonate (1.49 g, 0.008 moles) was stirred overnight at 45° C. The solvents were distilled off under reduced pressure (rotoevaporator). The crude product was dissolved in dichloromethane and added to cold ethyl ether. The precipitated product was filtered off and dried under reduced pressure. Yield 6.2 g. NMR (d$_6$-DMSO): 0.73 ppm (s, —CH$_3$ of OBO, 3H), 1.57 ppm (m, —CH$_2$—CH$_2$—CO—, 4H), 3.24 ppm (s, —OCH$_3$, 3H), 3.51 ppm (s, PEG backbone), 3.80 ppm (s, CH$_2$ of OBO, 6H).

Example 8

Formation of mPEG$_{(3,500\ Da)}$-butanoic Acid

The product of Example 7 (mPEG$_{(3,500\ Da)}$-butanoic acid, OBO ortho ester, 6.0 g) was dissolved in distilled water (60 ml). The pH of the solution was adjusted to 2 with 5% phosphoric acid and the solution was stirred for 15 minutes at room temperature. Next, the pH was readjusted to 12 with 1M sodium hydroxide and the solution was stirred for 2 hours. The pH of 12 was maintained by periodic addition of 1M sodium hydroxide. After two hours of stirring and maintaining a pH of 12, the pH was adjusted to 3 with 5% phosphoric acid and the product was extracted with dichloromethane. The extract was then dried with anhydrous magnesium sulfate and added to ethyl ether. The precipitated product was filtered off and dried under reduced pressure. Yield 5.6 g. NMR (d$_6$-DMSO): 1.72 ppm (q, CH$_2$—CH$_2$—COO—, 2H) 2.24 ppm (t, —CH$_2$—COO—, 2H), 3.24 ppm (s, CH$_3$O—, 3H), 3.51 ppm (s, PEG backbone).

Example 9

Formation of PEG$_{(5,000\ Da)}$-α-hydroxy-ω-propanoic Acid, OBO Ortho Ester Using Compound 7 as the Initiator for Polymerization Compound 7 (0.53 g, 0.00243 moles), tetrahydrofuran (THF, 200 ml), and potassium naphthalene 0.3 mol/1-tetrahydrofuran solution (10 ml, 0.00300 moles) were added to a glass reactor and stirred for three minutes in an argon atmosphere. Ethylene oxide (12.2 g, 0.277 moles) was added to this solution and the reaction mixture was stirred for 44 hours at room temperature. Next, the mixture was purged with argon and 0.1M phosphate buffer (pH=8, 100 ml) was added. The THF layer was separated and then discarded. Naphthalene was removed from the solution by ethyl ether extraction. Thereafter, the product was extracted with dichloromethane (3×50 ml). The extract was dried with anhydrous sodium sulfate and the solvent was distilled off under reduced pressure. Yield 11.7 g. NMR (d$_6$-DMSO): 0.73 ppm (s, —CH$_3$, 3H), 1.82 ppm (t, —CH$_2$—CO—, 2H), 3.51 ppm (s, PEG backbone), 3.80 ppm (s, CH$_2$ of OBO, 6H), 4.57 ppm (t, —OH, 1H).

Example 10

Formation of PEG$_{(5,000\ Da)}$-α-hydroxy-ω-propanoic Acid

The product of Example 9 (PEG$_{(5,000\ Da)}$-α-hydroxy-ω-propanoic acid, OBO ortho ester, 5.0 g) was dissolved in distilled water (75 ml). The pH of the solution was adjusted to 2 with 5% phosphoric acid and the solution was stirred 15 minutes at room temperature. Next, the pH was readjusted to 12 with 1M sodium hydroxide and the solution was stirred for two hours. The pH of the solution was maintained at a pH equaling 12 by periodic addition of 1M sodium hydroxide. After two hours of stirring and maintaining the pH at 12, the pH of the solution was adjusted to 3 with 5% phosphoric acid and the product was thereafter extracted with dichloromethane. The extract was then dried with anhydrous magnesium sulfate and added to ethyl ether. The precipitated product was filtered off and dried under reduced pressure. Yield 4.4 g. NMR (d$_6$-DMSO): 2.43 ppm (t, —CH$_2$—COO—, 2H), 3.51 ppm (s, PEG backbone), 4.58 ppm (t, —OH, 1H).

Example 11

Formation of mPEG$_{(5,000\ Da)}$-propanoic Acid, OBO Ortho Ester

A mixture of the product of Example 9 (PEG$_{(5,000\ Da)}$-α-hydroxy-ω-propanoic acid, OBO ortho ester, 4.0 g, 0.0008 moles), toluene (50 ml), 1.0M solution of potassium tert-butoxide in tert-butanol (8 ml, 0.008 moles), and methyl p-toluenesulfonate (1.49 g, 0.008 moles) was stirred overnight at 50° C. Next, the solvents were distilled off under reduced pressure (rotoevaporator). The crude product was then dissolved in dichloromethane and added to cold ethyl ether. The precipitated product was filtered off and dried under reduced pressure. Yield 3.6 g. NMR (d$_6$-DMSO): 0.73 ppm (s, —CH$_3$, 3H), 1.82 ppm (t, —CH$_2$—CO—, 2H), 3.24 ppm (s, CH$_3$O—, 3H), 3.51 ppm (s, PEG backbone), 3.80 ppm (s, CH$_2$ of OBO, 6H).

Example 12

Formation of mPEG$_{(5,000\ Da)}$-propanoic Acid

The product of Example 11 (mPEG$_{(5,000\ Da)}$-propanoic acid, OBO ortho ester, 6.0 g) was dissolved in distilled water (60 ml). The pH of the solution was the adjusted to 2 with 5% phosphoric acid and the solution was stirred for 15 minutes at room temperature. Next, the pH was readjusted to 12 with 1M sodium hydroxide and the solution was stirred for two hours. A pH of 12 was maintained by periodic addition of 1M sodium hydroxide. After two hours of stirring and maintaining a pH of 12, the pH of the solution was then adjusted to 3 with 5% phosphoric acid and the product was then extracted with dichloromethane. The extract was then dried with anhydrous magnesium sulfate and added to ethyl ether. The precipitated product was filtered off and dried under reduced pressure. Yield 5.6 g. NMR (d$_6$-DMSO): 2.43 ppm (t, —CH$_2$—COO—, 2H), 3.24 ppm (s, CH$_3$O—, 3H), 3.51 ppm (s, PEG backbone).

Example 13

Formation of mPEG$_{(20,000\ Da)}$-butanoic Acid

A solution of mPEG$_{(20,000\ Da)}$ (2.0 g, 0.0001 moles) (NOF Corporation) in toluene (30 ml) was azeotropically dried by distilling off 15 ml of toluene. 1.0M solution of potassium tert-butoxide in tert-butanol (0.80 ml, 0.0008000 moles) and the product of Example 2 [1-(3-bromopropyl)-4-methyl-2,6,7-trioxabicyclo[2,2,2]octane, 0.15 g, 0.0005973 moles] were added and the mixture was stirred overnight at 70° C. under argon atmosphere. The solvent was distilled off under reduced pressure and the residue was dissolved in distilled water (40 ml). The pH of the solution was adjusted to 2 with 5% phosphoric acid and the solution was stirred for 15 minutes at room temperature. Next, the pH was readjusted to 12 with 1M sodium hydroxide and the solution was stirred for two hours keeping the pH at 12 by periodic addition of 1M sodium hydroxide. Thereafter, the pH was adjusted to 3 with 5% phosphoric acid and the product was extracted with dichloromethane. The extract was dried with anhydrous magnesium sulfate and added to ethyl ether. The precipitated product was filtered off and dried under reduced pressure. Yield 1.6 g. NMR ($d_6$-DMSO): 1.72 ppm (q, $\underline{CH_2}$—$CH_2$—COO—) 2.24 ppm (t, —$CH_2$—COO—), 3.24 ppm (s, —$OCH_3$), 3.51 ppm (s, PEG backbone). Anion exchange chromatography: $mPEG_{(20,000)}$-butanoic acid 98.6%, m-PEG-20K 1.4%.

Example 14

Formation of 4-Bromohexanoate Ester of 3-Methyl-3-hydroxymethyloxetane (MW=251.12)

3-Methyl-3-hydroxymethyloxetane (20.5 g, 0.201 mole) was dissolved in anhydrous dichloromethane (250 ml) and pyridine (20.0 ml, 0.12 moles) was added. The solution was cooled to 0° C. and 4-bromohexanoyl chloride (42.7 g, 0.200 mole) dissolved in anhydrous dichloromethane (50 ml) was added dropwise over 20 minutes. Thereafter, the mixture was stirred overnight under argon atmosphere. Next, the reaction mixture was washed with water and dried with anhydrous magnesium sulfate. The solvent was then distilled off under reduced pressure. Yield 56.8 g. NMR ($d_6$-DMSO): 1.26 ppm (s, 3H), 2.07 ppm (m, 2H), 2.51 ppm (t, 2H), 3.56 ppm (t, 2H), 4.14 ppm (s, 2H), 4.24 ppm (d, 2H), 4.38 ppm (d, 2H).

Example 15

Formation of 1-(3-Bromopentyl)-4-methyl-2,6,7-trioxabicyclo[2,2,2]octane

The product of Example 14 (crude 4-bromohexanoate ester of 3-methyl-3-hydroxymethyloxetane, 20.1 g, 0.08 moles) was dissolved in anhydrous dichloromethane (100 ml), the solution was cooled to 0° C., and boron trifluoride diethyl etherate (2.5 ml, 0.022 moles) was added. The mixture was then stirred for 4 hours at 0° C. Triethylamine (12 ml) was added, the mixture was stirred for 15 minutes, and then the solvent was distilled off under reduced pressure. The crude product was then dissolved in ethyl ether (180 ml) and the solution was filtered to remove the solid impurities. Next, ether was distilled off and the product was distilled under reduced pressure (kugelrohr, 110-115° C., 0.05 mm Hg). Yield 15.0 g. NMR ($d_6$-DMSO): 0.74 ppm (s, 3H), 1.68 ppm (m, 2H), 1.88 ppm (m, 2H), 3.52 ppm (t, 2H), 3.81 ppm(s, 6H).

Example 16

Formation of $mPEG_{(2,000\ Da)}$-hexanoic Acid

A solution of $mPEG_{(2,000\ Da)}$ (2.0 g, 0.0010 moles) (NOF Corporation) in toluene (30 ml) was azeotropically dried by distilling off 15 ml toluene. 1.0M solution of potassium tert-butoxide in tert-butanol (0.60 ml, 0.0006000 moles) and the product of Example 16 [1-(3-bromopentyl)-4-methyl-2,6,7-trioxabicyclo[2,2,2]octane, 0.15 g, 0.0005973 moles] were added and the mixture was stirred overnight at 70° C. under argon atmosphere. The solvent was then distilled off under reduced pressure and the residue was dissolved in distilled water (40 ml). The pH of the solution was adjusted to 2 with 5% phosphoric acid and the solution was stirred for 15 minutes at room temperature. Next, the pH was readjusted to 12 with 1M sodium hydroxide and the solution was stirred for 2 hours while keeping the pH equal to 12 by periodic addition of 1M sodium hydroxide. The pH was then adjusted to 3 with 5% phosphoric acid and the product was extracted with dichloromethane. The extract was dried with anhydrous magnesium sulfate and added to ethyl ether. The precipitate was filtered off and dried under reduced pressure. Yield 1.6 g. NMR ($d_6$-DMSO): 1.72 ppm (q, $\underline{CH_2}$—$CH_2$—COO—) 2.24 ppm (t, —$CH_2$—COO—), 3.24 ppm (s, —$OCH_3$), 3.51 ppm (s, PEG backbone).

Example 17

Formation of $mPEG_{(5,000\ Da)}$—O—CH[$CH_2O(CH_2)_3COOH$]$_2$

A solution of $mPEG_{(5,000\ Da)}$—O—CH($CH_2OH$)$_2$ (2.0 g, 0.0004 moles) (prepared from $mPEG_{(5,000\ Da)}$-mesylate and 1,3-dibenzyloxy-2-propanol according to method described in published U.S. Patent Application US 2001/0011115) in toluene (30 ml) was azeotropically dried by distilling off 15 ml toluene. 1.0M solution of potassium tert-butoxide in tert-butanol (2.4 ml, 0.0024 moles) and 1-(3-bromopropyl)-4-methyl-2,6,7-trioxabicyclo[2,2,2]octane, 0.60 g, 0.0024 moles) (prepared as described in Example 2) were added and the mixture was stirred overnight at 70° C. under argon atmosphere. The solvent was distilled off under reduced pressure and the residue was dissolved in distilled water (30 ml). The pH of the solution was adjusted to 2 with 5% phosphoric acid and the solution was stirred for 15 minutes at room temperature. Next, the pH was readjusted to 12 with 1M sodium hydroxide and the solution was stirred for 1.5 hours while maintaining a pH equal to 12 by the periodic addition of 1M sodium hydroxide. Thereafter, the pH was adjusted to 3 with 5% phosphoric acid and the product was extracted with dichloromethane. The extract was then dried with anhydrous magnesium sulfate and added to ethyl ether. The precipitate was filtered off and dried under reduced pressure. Yield 1.6 g. NMR ($d_6$-DMSO): 1.72 ppm (q, $\underline{CH_2}$—$CH_2$—COO—) 2.24 ppm (t, —$CH_2$—COO—), 3.24 ppm (s, —$OCH_3$), 3.51 ppm (s, PEG backbone).

Example 18

Formation of $mPEG_{(5,000\ Da)}$-butanoic Acid

A solution of $mPEG_{(5,000\ Da)}$ (2.0 g, 0.0004 moles) (NOF Corporation) in toluene (20 ml) was azeotropically dried by distilling off solvent to dryness under reduced pressure. The dried material was dissolved in 15 ml of anhydrous toluene. 1.0M solution of potassium tert-butoxide in tert-butanol (1.2 ml, 0.0012 moles) and trimethyl 4-bromoorthobutyrate (Sigma-Aldrich, 0.25 g, 0.0011 moles) were added and the mixture was stirred overnight at 70° C. under argon atmosphere. The solvent was distilled off under reduced pressure and the residue was dissolved in distilled water (40 ml). The pH of the solution was adjusted to 2 with 5% phosphoric acid and the solution was stirred for 15 minutes at room temperature. Next the pH was readjusted to 12 with 1M sodium hydroxide and the solution was stirred for 2 hours keeping pH equal 12 by periodic addition of 1M sodium hydroxide. The pH was adjusted to 3 with 5% phosphoric acid and the product was extracted with dichloromethane. The extract was dried with anhydrous magnesium sulfate and added to ethyl ether. The precipitated product was filtered off and dried under reduced pressure. Yield 1.5 g. NMR (d$_6$-DMSO): 1.72 ppm (q, CH$_2$—CH$_2$—COO—) 2.24 ppm (t, —CH$_2$—COO—), 3.24 ppm (s, —OCH$_3$), 3.51 ppm (s, PEG backbone).

Example 19

Formation of mPEG-succinimidyl Butanoate

The product of Example 18 (mPEG$_{(5,000\ Da)}$-butanoic acid) is dissolved in methylene chloride to form a solution. N-hydroxysuccinimide and N,N-dicyclohexylcarbodiimide is then dissolved in 2 ml of methylene chloride and is added to the solution, which is then stirred overnight. Next, the mixture is filtered and the filtrate is concentrated under vacuum. The product is precipitated by addition of the filtrate to isopropanol and is then collected by filtration and dried under vacuum. The product is represented as follows:

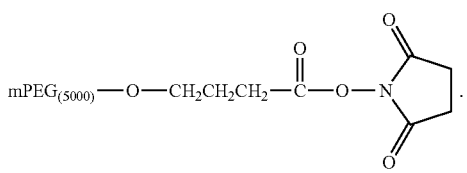

Example 20

Formation of PEGylated Lysozyme

Lysozyme serves as a protein model useful for conjugation reactions. Consequently, other active agent proteins can be substituted for lysozyme in this Example.

Lysozyme solution (4 ml, 3 mg/ml) in 50 ml of pH 6.5 buffer (50 mM sodium phosphate/50 mM NaCl) is added to 20 mg of N-succinimidyl ester of mPEG$_{(5,000\ Da)}$-butanoic acid (the product of Example 19, mPEG-succinimidyl butanoate). The progress of the reaction is monitored by capillary electrophoresis over a course of six hours to monitor the reaction. After the six hours, capillary electrophoresis shows evidence of PEGylated lysozyme.

Example 21

Formation of PEGylated Lysozyme

Lysozyme serves as a protein model useful for conjugation reactions. Consequently, other active agent proteins can be substituted for lysozyme in this Example.

The product of Example 18 (mPEG$_{(5,000\ Da)}$-butanoic acid) is dissolved in 20 ml of methylene chloride at room temperature and a solution is formed. The solution is then treated with 1,3-diisopropylcarbodiimide, 4-dimethylaminopyridine and lysozyme at 0° C. The reaction solution is then warmed to room temperature after several hours and kept at room temperature for about 16 hours. The reaction mixture is then washed with hydrochloric acid, dried and evaporated to yield the conjugated product.

What is claimed is:

1. A polymer having the following structure:

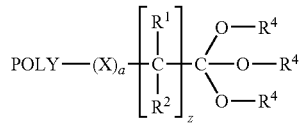

wherein:
POLY is a water-soluble polymer segment having a nominal average molecular weight of from about 2,000 daltons to about 25,000 daltons;
(a) is either zero or one;
X, when present, is a spacer moiety;
(z) is an integer from 1 to 24;
R$^1$, in each occurrence, is in dependently H or an organic radical selected from the group consisting of alkyl, substituted alkyl, alkenyl, substituted alkenyl, alkynyl, substituted alkynyl, aryl, and substituted aryl;
R$^2$, in each occurrence, is independently H or an organic radical selected from the group consisting of alkyl, substituted alkyl, alkenyl, substituted alkenyl, alkynyl, substituted alkynyl, aryl, and substituted aryl; and
each R$^4$ is a either (i) an organic radical independently selected from the group consisting of alkyl, substituted alkyl, alkenyl, substituted alkenyl, alkynyl, substituted alkynyl, aryl, and substituted aryl, or (ii) one or more atoms that combine with another R$^4$ or the remaining R$^4$ moieties to form a cyclic ortho ester structure.

2. The polymer of claim 1, wherein (z) equals three and the polymer has the following structure:

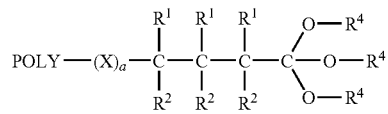

3. The polymer of claim 2, wherein each occurrence of R$^1$ and R$^2$ is H.

4. The polymer of claim 2, wherein the R$^1$ attached to the carbon α to the carbon in the ortho ester moiety is alkyl, all other R$^1$ variables are H, and all R$^2$ variables are H.

5. The polymer of claim 1, wherein POLY is selected from the group consisting of a poly(alkylene oxide), poly(vinyl pyrrolidone), poly(vinyl alcohol), polyoxazoline, poly(acryloylmorpholine), and poly(oxyethylated polyol).

6. The polymer of claim 5, wherein POLY is a poly(alkylene oxide).

7. The polymer of claim 6, wherein the poly(alkylene oxide) is a poly(ethylene glycol).

8. The polymer of claim 7, wherein the poly(ethylene glycol) is terminally capped with an end-capping moiety.

9. The polymer of claim 8, wherein the end-capping moiety is independently selected from the group consisting alkoxy, substituted alkoxy, alkenyloxy, substituted alkenyloxy, alkynyloxy, substituted alkynyloxy, aryloxy, substituted aryloxy, and hydroxy.

10. The polymer of claim 9, wherein the end-capping moiety is alkoxy.

11. The polymer of claim 10, wherein the alkoxy is methoxy.

12. The polymer of claim 9, wherein the end-capping moiety is hydroxy.

13. The polymer of claim 7, wherein the poly(ethylene glycol) has a nominal average molecular weight of from about 5,000 daltons to about 20,000 daltons.

14. The polymer of claim 1, wherein (a) equals zero.

15. The polymer of claim 1, wherein (a) equals one.

16. The polymer of claim 15, wherein X is independently selected from the group consisting of —O—, —S—, —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH2CH2)$_j$—, —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)-,bivalent cycloalkyl group, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20.

17. The polymer of claim 1, wherein each R$^4$ combines with another R$^4$ or the remaining R$^4$ moieties to form an ortho ester cyclic structure.

18. The polymer of claim 17, wherein each R$^4$ combines with another R$^4$ or the remaining R$^4$ moieties to form an ortho ester cyclic structure selected from the group consisting of

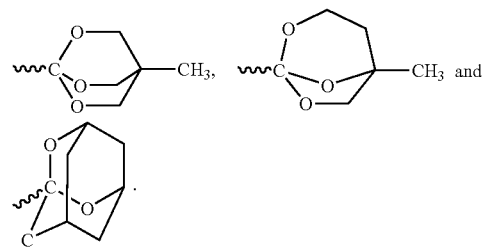

19. The polymer of claim 1, selected from the group consisting of

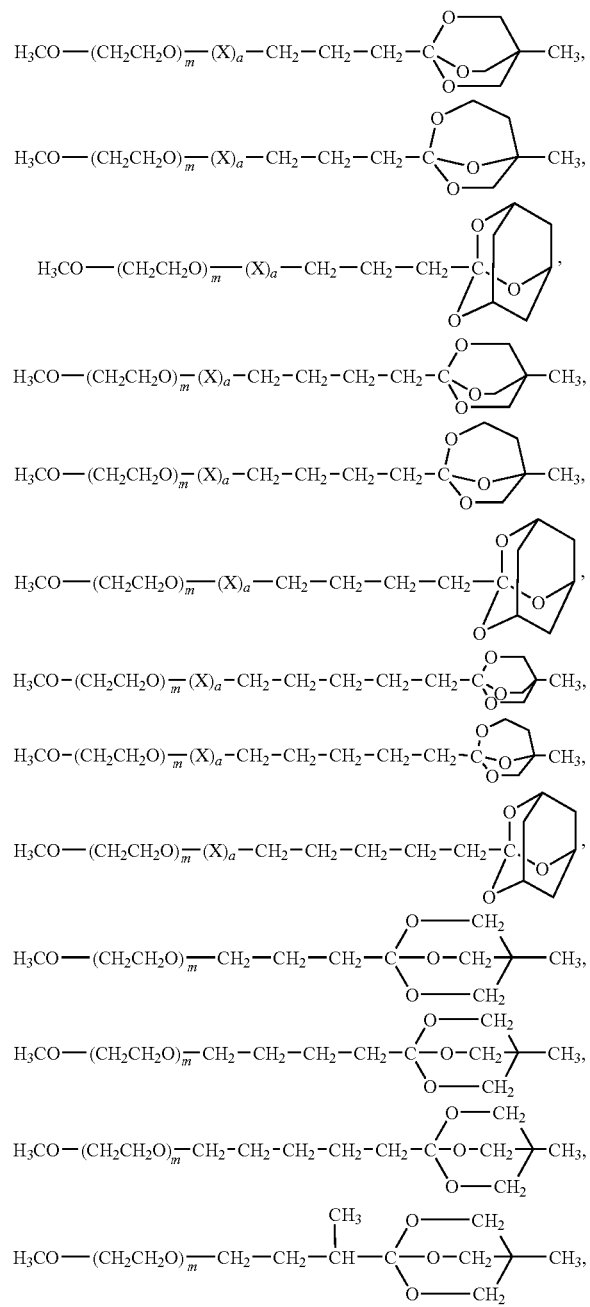

-continued
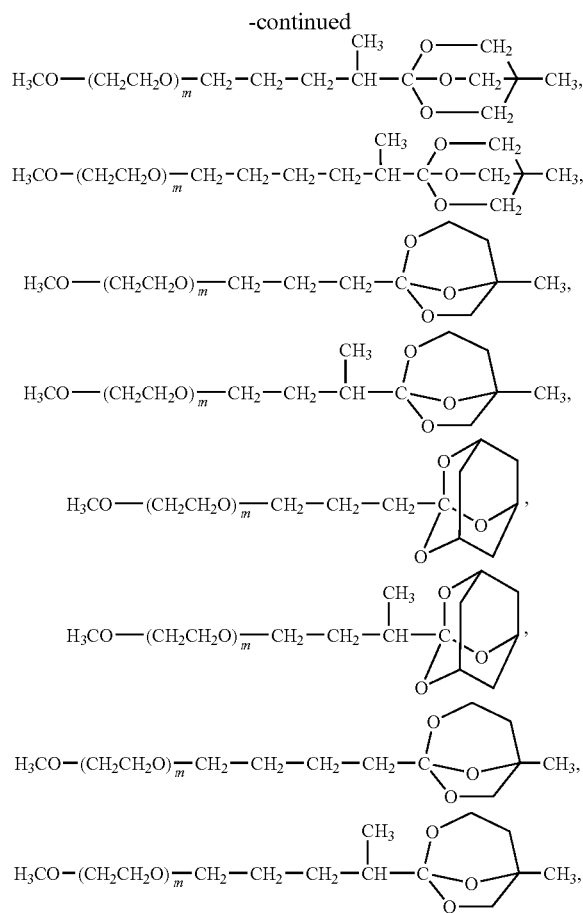
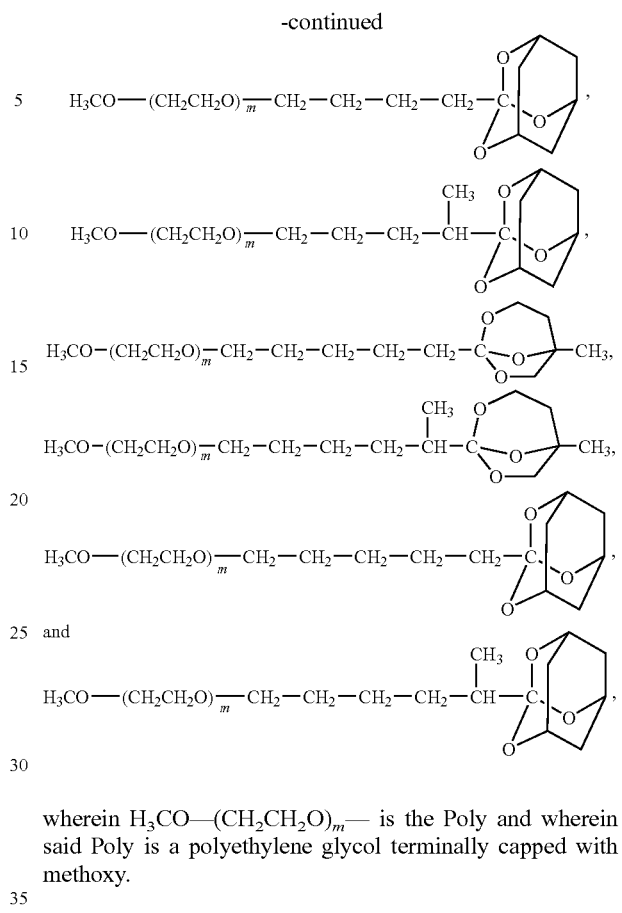
wherein $H_3CO-(CH_2CH_2O)_m-$ is the Poly and wherein said Poly is a polyethylene glycol terminally capped with methoxy.
* * * * *